(12) United States Patent
Catto et al.

(10) Patent No.: US 11,213,612 B2
(45) Date of Patent: Jan. 4, 2022

(54) HYBRID SCAFFOLD SUITABLE FOR REGENERATING ANIMAL TISSUES AND PROCESS FOR PRODUCING THE SCAFFOLD

(71) Applicant: Bioengineering Laboratories S.r.l., Cantu (IT)

(72) Inventors: Valentina Ilaria Maria Catto, Brugherio (IT); Sebastiao Nicolau Dentinho Van Uden, Sintra (PT); Francesco Giovanni Greco, Cantu (IT); Davide Meroni, Lissone (IT); Stefania Adele Riboldi, Milan (IT)

(73) Assignee: DIALYBRID S.R.L., Milan (IT)

( * ) Notice: Subject to any disclaimer, the term of this patent is extended or adjusted under 35 U.S.C. 154(b) by 99 days.

(21) Appl. No.: 16/394,662

(22) Filed: Apr. 25, 2019

(65) Prior Publication Data

US 2019/0247545 A1    Aug. 15, 2019

Related U.S. Application Data

(63) Continuation-in-part of application No. PCT/EP2017/001263, filed on Oct. 27, 2017.

(30) Foreign Application Priority Data

Oct. 28, 2016  (EP) .................................. 16425100

(51) Int. Cl.
*A61L 27/50*  (2006.01)
*A61L 27/26*  (2006.01)
(Continued)

(52) U.S. Cl.
CPC .............. *A61L 27/507* (2013.01); *A61F 2/24* (2013.01); *A61L 27/047* (2013.01);
(Continued)

(58) Field of Classification Search
CPC .... A61L 27/507; A61L 27/3604; A61L 27/40; A61F 2/24
See application file for complete search history.

(56) References Cited

U.S. PATENT DOCUMENTS 9,102,916 B2 *   8/2015  Kaplan ................. A61L 27/227
2004/0199241 A1* 10/2004  Gravett ................... A61L 31/14
                                                 623/1.13

FOREIGN PATENT DOCUMENTS

| CN | 101214393 B | 10/2010 |
| CN | 102499800 A | 6/2012 |
| CN | 102817105 A | 12/2012 |
| CN | 101708344 B | 1/2013 |

(Continued)

OTHER PUBLICATIONS

Database WPI week 201430, Thomson Scientific, AN 2014-G41246, 2 pages, XP002768815.
(Continued)

*Primary Examiner* — Suba Ganesan
(74) *Attorney, Agent, or Firm* — Lucas & Mercanti, LLP

(57) ABSTRACT

A hybrid scaffold is disclosed which is made of materials that define peripheral layers designed to interface with the tissues in the implant site and one or more intermediate layers. The materials are combined to give the scaffold mechanical properties suitable for withstanding the stresses of the implant site. The materials are fibroin for the peripheral layers and polyurethane combined with fibroin for each intermediate layer.

18 Claims, 10 Drawing Sheets

(51) Int. Cl.
    *A61L 27/22*     (2006.01)
    *A61F 2/24*     (2006.01)
    *A61L 27/04*     (2006.01)
    *A61L 27/34*     (2006.01)
    *A61L 27/36*     (2006.01)
    *A61L 27/48*     (2006.01)
    *A61L 33/18*     (2006.01)
    *A61M 1/36*     (2006.01)
    *D01D 5/00*     (2006.01)
    *D01D 5/34*     (2006.01)
    *A61F 2/06*     (2013.01)

(52) U.S. Cl.
CPC ............. *A61L 27/227* (2013.01); *A61L 27/26* (2013.01); *A61L 27/34* (2013.01); *A61L 27/3687* (2013.01); *A61L 27/48* (2013.01); *A61L 33/18* (2013.01); *A61M 1/3655* (2013.01); *D01D 5/003* (2013.01); *D01D 5/34* (2013.01); *A61F 2002/065* (2013.01); *A61F 2240/001* (2013.01); *A61L 2420/02* (2013.01); *A61L 2420/06* (2013.01); *A61L 2430/20* (2013.01); *D10B 2211/22* (2013.01); *D10B 2331/10* (2013.01); *D10B 2509/06* (2013.01)

(56) References Cited

FOREIGN PATENT DOCUMENTS

| CN | 101874751 B | 7/2013 |
|---|---|---|
| CN | 103585674 A | 2/2014 |

OTHER PUBLICATIONS

Yongzhen, Tao, et al., "Rheological and Mechanical Behavior of Silk Fibroin . . . ", Polymers, vol. 8, No. 3, 94, pp. 1-18, 2016.

P. Petrini, et al., "Silk Fibroin-Polyurethane Scaffolds for Tissue Engineering", Journal of Materials Science: Materials in Medicine, pp. 849-853, 2001.

Database WPI week 201251, Thomson Scientific, AN2012-J41209, 1 page, XP002768816.

Database WPI week 201378, Thomson Scientific, AN 2013-G66898, 4 pages, XP002768817.

Sebastiao van Uden, et al., "A Novel Hybrid Silk-Fibroin/Polyurethane Three-Layered . . . ", Biomed. Mater. vol. 14, pp. 1-17, 2019.

Sebastiao van Uden, et al., "Electrospun Fibroin/Polyurethane Hybrid Meshes: Manufacturing . . . ", Society for Biomaterials, pp. 1-11, 2018.

International Search Report and Written Opinion for Corresponding International Application No. PCT/EP2017/001263 (10 Pages) (dated Dec. 11, 2017).

\* cited by examiner

Table II

|     | $C_i$         | $T_g$ | $T_c$ | $T_d$            |
|-----|---------------|-------|-------|------------------|
| FF  | 31.4% ± 3.3%  | 181.3 | 217   | 292              |
| FFS | 39.4% ± 2.1%  | 182.6 | 230   | 287              |
| PP  | –             | –     | –     | 369              |
| PFS | –             | –     | –     | 354              |
| BFS | 37.9% ± 0.5%  | 182.6 | 226   | 1°, 293 2°, 358  |
| ENC | 28.4% ± 0.8%  | 182.6 | 217   | 1°, 295 2°, 357  |
| EtOH| 40.5% ± 0.9%  | 202   | 223   | 1°, 294 2°, 324  |
| MeOH| 39.6% ± 1.1%  | 202   | 227   | 1°, 295 2°, 339  |

FIG. 13

HYBRID SCAFFOLD SUITABLE FOR REGENERATING ANIMAL TISSUES AND PROCESS FOR PRODUCING THE SCAFFOLD

CROSS-REFERENCE TO RELATED APPLICATIONS

This application is a continuation-in-part of PCT Application Serial No. PCT/EP2017/001263, filed Oct. 27, 2017, which in turn claims the benefit of priority from European Patent Application No. 16425100.1, filed Oct. 28, 2016, the contents of each of which are incorporated herein by reference.

FIELD OF THE INVENTION

The applicant informs that the project leading to this application has received funding from the European Union's Horizon 2020 research and innovation program under the Marie Sklodowska-Curie grant agreement No. 642458.

The searches carried out under that program led to an invention in the field of scaffolds suitable for regenerating animal tissues and of a process for producing the scaffold, the latter being in the field of the scaffolds used for repairing damaged anatomical areas in the cardio-vascular apparatus (for example the myocardium, the heart valves and blood vessels) and in the field of the so-called vascular accesses (or arteriovenous grafts), i.e. those vascular prostheses that are used to enter the blood stream via percutaneous access.

BACKGROUND OF THE INVENTION

Scaffolds are known suitable for leading to, encouraging and supporting the regeneration of native compromised tissues. Such scaffolds are generally produced from natural materials (such as collagen, elastin, fibrin, gelatin, fibroin, chitosan, hyaluronic acid, etc.) or synthetic materials (as PCL—polycaprolactone, PGA—polyglycolic acid, PLA—polylactic acid, PTFE—polytetrafluoroethylene, PET—polyethylene terephthalate, polyurethanes, etc.) in order to confer mechanical properties adequate to those of the tissues to be replaced, on the time and in the site of implantation. With the progress in the repairing process and the consequent generation of new biological tissues, such scaffolds are usually reshaped and degraded, totally or partially, to be incorporated in or replaced by newly formed tissue.

One of the main challenges in designing a scaffold, then, is just to gather the biocompatibility properties and the mechanical properties of the material with its degradative capacities, so that the scaffold can accompany—not hinder—the repairing processes. In this context, natural materials generally appear to excel for their properties of biocompatibility, degradability and ability to reproduce the native structures, favoring the integration with host cells, while synthetic materials offer better control of mechanical properties of the scaffold, which is crucial for the application in tissues subjected to continuous mechanical stress such as those typical of the cardiovascular system. A number of attempts have been made, therefore, to combine natural materials and synthetic materials, in many forms and in different structural organizations, in order to produce scaffolds that could afford the advantages of both classes of materials.

For example, fibroin and polyurethane scaffolds were generated, both in the form of continuous membranes and of fibrous membranes, mixing the two materials in solution or in suspension, or by the application of a fibroin coating on a polyurethane-based structure. More specifically, in the field of vascular prostheses, various technologies, such as electrospinning, dipping, gas foaming, etc., have been employed to produce hybrid tubular structures in which natural macromolecules (such as fibroin, collagen, elastin, etc.) are combined with synthetic polymers (such as polyurethanes, polyvinyl alcohol, polycaprolactone, etc.).

In the context of vascular accesses for hemodialysis, instead, grafts are commonly used to connect an arterial vessel with a venous vessel, in order to ensure the ability to perform the dialysis treatment, and they are generally composed of synthetic and non-degradable materials only, such as PTFE (polytetrafluoroethylene), polyethylene terephthalate, polyurethane. The reason for this peculiarity lies in the fact that for the arteriovenous fistulas it is critical the need to ensure sufficient mechanical properties to support the stress typical of the particular application, namely, in addition to the cyclic ones typical of the blood stream, those due to the repeated puncture by using dialysis needles.

Among the various documents in the state of the art describing scaffolds made of natural and synthetic materials, there is Patent No CN 101214393 B that discloses a multilayer vascular prosthesis produced by electrospinning, comprising an inner layer of natural material and an outer layer made of synthetic material.

Patent No CN 101708344 B discloses a multilayer vascular prosthesis produced by electrospinning, comprising an inner layer of natural material and an outer layer of polyurethane.

Patent No CN 101874751 B covers a multilayer scaffold produced by "particle removal". The layers are obtained from polymeric materials (degradable and non-degradable), inorganic, biologically derived (known in the field, including fibroin among those degradable and polyurethane among those non-degradable) or mixtures thereof, and the different layers can have composition different each from the other.

Further documents found in the prior art are:

Patent application No CN 103585674 A discloses a method for preparing a porous fibroin fiber scaffold in which a synthetic polymer material (e.g. PU) is added to the fibroin.

Document by YONGZHEN TAO ET AL: "Rheological and Mechanical Behavior of Fibroin Reinforced Waterborne Polyurethane", POLYMERS, vol. 8, no. 3, 21 Mar. 2016 (2016-03-21), page 94, XP55360549, DOI: 10.3390/polym8030094 discloses the use of fibroin-reinforced polyurethane for tissue engineering.

Document by P Petrini ET AL: "Fibroin-polyurethane scaffolds for tissue engineering", Journal of Materials Science: Materials in Medicine, 1 Dec. 2001 (2001-12-01), pages 849-853, XP55360564, Boston DOI: 10.1023/A:1012847301850 Retrieved from the Internet: URL: https://rd.springer.com/content/pdf/10.1023/A:1012847301850.pdf [retrieved on 2017 Mar. 30] discloses polyurethane scaffolds having a silk-fibroin coating and their use for tissue engineering.

Patent No CN 102499800 A discloses small-diameter vessel repairing vascular support with a PCL fibroin inner net and a middle layer sleeved with a fibroin tube.

Patent application No CN 102817105 A discloses a method for preparing a synthetic polymer-natural polymer composite fiber with a core shell structure by coaxial electrostatic spinning. The method utilizes the synthetic polymer (e.g. polyurethane) as shell and the natural polymer (e.g. fibroin) as core.

DRAWBACKS IN THE PRIOR ART

The greatest difficulties in the manufacture of hybrid scaffolds, composed of synthetic and natural materials, are mainly of a practical and experimental type, since often the treatments needed to process the synthetic materials (e.g. the solubilization in aggressive solvents) are detrimental for the purpose of a stable conformation of natural macromolecules, which are denatured or degraded during the process, partly losing their properties. In other cases, the treatments necessary to stabilize the natural materials (such as, in the case of fibroin, crystallization) determine in the different phases—natural and synthetic—reactions of different entities (for example, in the aforementioned case of the crystallization, volumetric shrinkage) that prevent an excellent coalescence between the materials. By the term coalescence it is intended the merging between materials (or layers of materials), due to intimate contact, binding, weaving, intersection, intermingling, or other forms of physical connection. Many attempts to cover synthetic materials with natural materials, aimed at increasing the integration of the scaffold with the host organism, then failed because of the scarce coalescence at the interface between the two materials, which determines the detachment of the coating.

Consequently, the greatest issues to be improved in the known scaffolds concern:

a) the integration of the scaffold with the surrounding biological tissues, b) the maintenance of the intrinsic elastic properties of the synthetic polymer, that are essential for cardiovascular applications, and for applications in the field of hemodialysis vascular accesses, and c) the stability in combining natural and synthetic polymer, that is needed to avoid that post-processing treatments and/or operational conditions determine the delamination and/or the separation of the two materials.

As far as the above cited documents, the following deficiencies were found with respect to the above issues.

Patent application No CN 103585674 A wouldn't solve the problem to improve the integration properties of the scaffold with the surrounding biological tissues, as the synthetic polymer would be present at the interface of the scaffold with the surrounding biological tissues, impairing the scaffold integration.

Document YONGZHEN TAO ET AL discloses a technique in which the addition of fibroin significantly affects the elastic properties of the polyurethane inducing strengthening and toughening. Moreover, the proposed solution wouldn't solve the problem to improve the integration properties of the scaffold with the surrounding biological tissues as the synthetic polymer would anyway be present at the interface of the scaffold with the surrounding biological tissues.

Document P Petrini ET AL discloses a technique in which fibroin only is present at the scaffold-tissue interface, but it fails in analyzing the effects of the fibroin coating on the mechanical properties of polyurethane foams and it surely admits that there is a mismatch of the mechanical properties of the polyurethane substrate (elastomeric) and the protein coating.

Patent No CN 102499800 A discloses a technique which apparently succeeds in combining fibroin and PCL, but no mention is made of the elastic properties of the synthetic polymer and a "suture connection" seems to be required to allow for an external tube of fibroin to improve the integration properties with the outer (not with the inner) tissues.

Patent application No CN 102817105 A discloses a technique which indeed combines natural and synthetic material, but fails in providing the desired integration properties with the surrounding biological tissues (the synthetic material, and not the natural material is present at the interface with the surrounding tissues) and in retaining the intrinsic elastic properties of the polyurethane (no mention is made of the mechanical properties in the coaxially spun fiber).

In the specific case of hemodialysis vascular accesses, there are a number of drawbacks associated with the clinical use of prostheses made of synthetic materials:

poor resemblance of the morphological and mechanical features of the prosthesis with those of native blood vessels;

arising from the previous point: formation of neointimal hyperplasia at the anastomosis and subsequent stenosis or occlusion of the prosthesis and incidence of thrombotic phenomena;

poor integration of the prosthesis with surrounding biological tissues and poor or no remodeling capacity, arising from the previous point: chronic inflammation in the prosthesis area.

In addition to the drawbacks recalled above, the known synthetic vascular accesses used in the hemodialysis field also suffer from:

failure to ensure a prompt sealing of the puncture site, once the needle is removed, resulting in hemostasis delay;

infectious phenomena.

OBJECTS AND SUMMARY OF THE INVENTION

A first object of the invention is a scaffold made of natural and synthetic materials suitable for regenerating cardiovascular tissues or for use as hemodialysis vascular access devoid of the prior art drawbacks and so suited to:

a) provide integration with the surrounding biological tissues;

b) retain the intrinsic elastic properties that are essential for cardiovascular applications and for applications in the field of hemodialysis vascular accesses, and c) stably combine natural and synthetic materials in order to avoid that postprocessing treatments and/or operational conditions cause the delamination and/or the separation of the two materials.

This object is achieved by a combination of a natural material, fibroin, with a synthetic material, a polyurethane, and conferring to the scaffold a specific multilayer structural organization.

Another object of the invention is to provide scaffolds so shaped that are suitable for replacing atrioventricular or semilunar heart valves and vascular bifurcated tracts affected by pathologies.

A second object of the invention is a process, particularly suited to industrial scale, for producing the scaffolds defined in the first object.

It is started by saying that, in the following of the present description, by fibroin it is intended silk fibroin and the blood is considered to be a tissue of the animal body and considering that "porosity" is defined as the percentage of empty space in a solid.

The first object of the invention is a hybrid scaffold produced by successively depositing, on a support of suitable shape, materials such that generate:

peripheral layers designed to interface with the tissues in the implant site and suitable for improving the integration of the scaffold with the cells of the host organism;

one or more intermediate layers where materials are combined to give the scaffold mechanical properties suitable to withstand the typical stresses of the implant site, the materials being:

fibroin for the peripheral layers, polyurethane combined with fibroin for each intermediate layer, so that the scaffold comprises fibroin in the peripheral layers which confer the scaffold the property of integration with the surrounding biological tissues, and polyurethane combined with fibroin in the one or more intermediate layers that determine the stable coalescence between adjacent layers while maintaining the intrinsic elastic properties conferred to the scaffold by the polyurethane in said intermediate layers.

Indeed, applicant's direct experience confirmed that, in the absence of fibroin in the one or more intermediate layers, it is problematic to ensure coalescence between the different materials and different layers within the scaffold. In fact, as shown in the graph FIG. 5, the characteristic "Load/Extension" curve of a sample made by electrospinning a layer of fibroin, electrospinning a subsequent layer of polyurethane and then electrospinning a second layer of fibroin ("PU core" plot) showed a typical saw-toothed morphology, precisely due to delamination between layers. The applicants were able to overcome this issue, that would have impaired the integrity and the mechanical behavior of the final scaffold, only by adding fibroin to the inner layers of the scaffold (see for comparison the "SF-PU blend core" plot in the same graph, showing a neater and sharper behavior, typical of a continuum).

The structural organization, namely the shape imparted to the scaffold defined above, is of four types:

a tubular scaffold suitable for being used as a vascular prosthesis or as a vascular access;

a lamellar scaffold suitable for regenerating cardio-vascular tissues and in particular the myocardium;

a shapeable scaffold of complex shape and suitable for replacing atrioventricular or semilunar heart valves or their parts, such as the annulus, valvular sinuses, flaps; and a scaffold in the shape of bifurcated duct in one piece suitable for replacing bifurcated vascular tracts suffering conditions such as stenosis and aneurysms, for example at iliac, carotid or coronary position.

Indeed, several studies were conducted by the applicants in order to ensure the possibility to tune the mechanical properties of the scaffold to the different anatomical districts cited above. Evidences were obtained through experiments that, by varying the respective ratios of fibroin and polyurethane in the one or more intermediate layers, the scaffold elasticity can be modulated, maintaining the coalescence between the materials and the layers. As shown in the graphs depicted in FIG. 6 below, referred to electrospun meshes with intermediate layers of varied compositions (75% fibroin-25% polyurethane or 50% fibroin-50% polyurethane or 25% fibroin-75% polyurethane), increasing the polyurethane percentage allows achieving higher deformations at break, while increasing the percentage of fibroin stiffens the mesh.

The tuneability of the mechanical properties described above, besides allowing the maintenance of the intrinsic elastic properties of the polyurethane, essential for cardiovascular applications, also enables tailoring the properties of the scaffold to the specific site of implantation (e.g. cardiac valve, rather than cardiac muscle, or blood vessel), which is crucial to avoid the deleterious mismatch of elasticity between native tissues and scaffold, known to be one of the greatest causes for lack of integration of the scaffold itself.

The second object of the invention is a process in which the intermediate layer or the intermediate layers are generated from a mixture of fibroin and polyurethane (mixture prepared separately and then treated to form the scaffold), or such to hold separated and side by side fibroin and polyurethane materials, or mixture fibroin/polyurethane into distinct phases and in very varied forms (for example in the form of separate fibers, fiber where the materials are arranged coaxially to each other, or matrix and inclusions).

The process used to produce the hybrid scaffold is preferably the electrospinning that in general allows to obtain continuous filaments of nano or micro-metric diameter and, in this case, allows to produce nano or micro-fibrous matrices that resemble for their effectiveness to extracellular matrix (ECM) of native tissues. With known techniques in which composite collectors are used in separate stages, the electrospinning also enables to obtain a scaffold of complex shape comprising bifurcated ducts and atrioventricular or semilunar valves.

The invented process, particularly suited to industrial scale, basically comprises:

the electrospinning of at least a first layer of solubilized fibroin on a collector of a suitable shape for the desired scaffold;

the subsequent deposition on the first layer of one or more intermediate layers composed of fibroin and polyurethane materials combined, for example, by means of electrospinning a mixture of fibroin and polyurethane, by means of electrospinning of distinct fibers of fibroin and polyurethane, by means of electrospinning of solutions of fibroin and polyurethane arranged coaxially to each other, or by other techniques such as solvent casting, dipping, particulate leaching, hydrogelation, lyophilization, additive manufacturing, making it possible to obtain a composite structure of matrix and inclusions, a hydro gel, a sponge or a controlled porosity films; and the electrospinning of at least a last layer of solubilized fibroin, deposited on the intermediate layers or layer, said process being suitable in an industrially-sustainable context, to achieve scaffolds where fibroin and polyurethane are completely integrated, non-degraded and non-denatured.

Optionally, the intermediate layers of fibroin and polyurethane are produced with the mixture of said two materials solubilized in the following conditions:

a) in a solvent or combination of solvents suitable for solubilizing both or each of the two materials, such as (but not only) water, formic acid, trifluoroacetic acid, chloroform, dichloromethane, hexafluoroisopropanol, dimethylformamide, cyclohexanone, dimethylacetamide, methylene chloride, tetrahydrofuran, dimethylsulfoxide, if necessary using additives (e.g. salts such as lithium bromide, lithium chloride, lithium iodide) to improve the solubilization of the materials;

b) at a concentration suitable for the porosity of the scaffold under production (lower concentration to achieve higher porosity) and for the following processing method (for example using preferably highly volatile solvents, if the mixture is then processed by electrospinning, in order to promote a better evaporation of the solvent), in a suitable weight ratio and under suitable environmental conditions (for example, by increasing the temperature above room temperature in order to promote the complete solubilization of the materials, while protecting them from denaturation and degradation);

c) with a sequence of operations according to the characteristics of the materials and of the solvents in use (sequence meaning the order in which the various reagents are put in contact with each other in order to avoid any precipitation of previously solubilized materials, or undesired reactions).

For example, fibroin and polyurethane in a ratio of 1:1 are solubilized in formic acid and dichloromethane in the ratio 3:2 to obtain a solution with 2% fibroin and 2% polyurethane, by solubilizing the fibroin in formic acid and the polyurethane in formic acid and dichloromethane and then combining the two solutions.

Optionally, the scaffold is subjected to known physical-chemical treatments, aimed at washing out solvent residuals and/or at inducing fibroin crystallization. The measures which may be taken include exposure to organic solvents or to solutions of organic solvents and water or to pure water, application of mechanical stress, thermal treatments.

It should be considered that the process for the production of the scaffold was fine-tuned as a result of studies and experiments, focused on finding the best conditions to treat fibroin and polyurethane in an industrially-sustainable context, without inducing denaturation and/or degradation of the materials, and ensuring complete coalescence between them in the final scaffold.

For example, in the above-cited case of preparing a mixture of fibroin and polyurethane, several attempts were tried to avoid the use of HFP (hexafluoroisopropanol) which, despite being broadly used to simultaneously dissolve fibroin and synthetic polymers (see for example the cited documents CN 103585674 A and CN 102499800 A), is characterized by extreme volatility and high cost, thus being scarcely compatible with industrial procedures.

After several trials (e.g. with dimethylacetamide, dimethylformamide, and chloroform), it was found that a combination of solvents such as trifluoroacetic acid and dichloromethane or formic acid and dichloromethane (3:2) can solubilize both fibroin and polyurethane avoiding precipitations, denaturations and degradations, being suitable for electrospinning in an industrially-sustainable context. By using formic acid and dichloromethane (3:2), for example, evidences were found that the mixture can be processed by electrospinning to produce good-quality meshes (shown in FIG. 7) resembling native extracellular matrix, where fibroin and polyurethane are fully intermingled and completely coalescent, so as to avoid local delamination and/or detachment between the different materials.

Indeed, evidences were obtained through experiments that the invented process is also robust enough to allow for a broad variation of the fibroin/polyurethane respective ratio in the one or more intermediate layers, so as to enable the above mentioned fine tuning of the mechanical properties of the scaffold, without loss of coalescence between materials and layers. Interestingly, the changes in the respective ratios of fibroin and polyurethane in said layers did not appear to significantly affect the average stress at break of the scaffolds, confirming that the process allows for good coalescence between the two materials and integrity of the microstructure.

Such a stable coalescence between layers was found in the scaffolds also after subjecting them to crystallization treatments (e.g. in a solution of methanol and water, or in series of degrading ethanol/water solutions), assessing that the process for the production of the scaffolds allows fibroin and polyurethane to have complete coalescence, so that they in unison respond to treatments that usually determine a detachment/delamination between the two materials (due to volumetric shrinkage of fibroin and not of polyurethane upon crystallization).

Optionally, also, the inner surface of the scaffold or the entire scaffold are subjected to physical-chemical treatments, using compounds and techniques known in the field of bioengineering, in order to improve the hemocompatibility and antimicrobial properties of the scaffold itself and its permeability to blood plasma. The measures which may be taken singly or in two or more together are the following:

a) the inner surface of the scaffold is coated or functionalized with heparin, warfarin, statin, compounds derived from fish oil, graphite or other carbon-based compounds, anti-thrombin, argatroban, fibronectin, sulphate-based coatings, or subjected to physical processes such as gas plasma treatments and ultraviolet light, in order to improve the hemocompatibility properties.

b) the scaffold is completely or partly impregnated or coated with albumin or other compounds with the purpose of controlling the permeability of the blood plasma.

c) the scaffold is completely or partially coated or functionalized with silver, with antimicrobial peptides or antibiotic and antiviral molecules, or generated from fibroin genetically modified, in order to increase the antimicrobial properties.

Advantages of the Invention

A "constructive or process" advantage of the invention mainly resides in the fact that the industrially-sustainable treatment of the fibroin and polyurethane to produce each intermediate layer allows an excellent coalescence of the two materials within those layers themselves and with the peripheral layers that do not delaminate from each other, as in the case of the coating, nor it determines damage or denaturation of fibroin and polyurethane during processing.

In addition to this, an "operative" advantage of the invented multi-layered scaffold lies in the fact that the scaffold joins the advantages of a natural and biodegradable material (e.g. the biocompatibility, in vivo degradability, the possibility of being remodeled) with those of a synthetic and non-degradable material (e.g. the greater stability of the mechanical properties and, specifically for the polyurethane, the high elasticity). In the general case of a cardiovascular application, the polyurethane presence would improve the elasticity of the matrix, resulting in an excellent mechanical performance with respect to the typical stress in the implant site, as well as greater resistance to suture.

More specifically, in case of using the scaffold as a vascular access, the fibroin and polyurethane hybrid scaffold offers the following advantages with respect to the implants presently used in the clinics:

thanks to the fibroin: a better reproduction of the morphological characteristics of native blood vessels, resulting in facilitating the access of the host body cells and thus in improving the integration and remodeling of the prosthesis, in a decrease of the chronic inflammation due to the implantation, in a reduction in the formation of neointimal hyperplasia at the anastomosis and, ultimately, in lower risk of stenosis and thrombosis. In this regard, it has already been shown in the scientific literature that electrospun vascular prostheses in fibroin are totally degraded and replaced by natural vascular tissue in just 7 days after implantation in an animal model (rat) [reference source Cattaneo I, Figliuzzi M, Azzollini N, V Catto, Fare S, M C Tanzi, Alessandrino A, Freddi G, Remuzzi A. In vivo regeneration of elastic lamina on fibroin biodegradable vascular scaffold. Int J Artif Organs 2013 March; 36 (3): 166-74-];

thanks to the polyurethane: a greater elasticity of the wall of the prosthesis, which allows quick sealing of the dialysis puncture site, and, consequently, a better hemostasis. In this regard, it is known that electrospun vascular prostheses in polyurethane have undoubted advantages when used as vascular access for dialysis, just for said reason, thanks to the fibroin: the prosthesis could enjoy moderate antimicrobial properties (this aspect being currently the object of scientific research) and thus be less susceptible to infection.

BRIEF DESCRIPTION OF THE DRAWINGS

FIG. 13 is a Table providing data related to the physicochemical analysis of Samples PP, PFS, FF, FFS, BFS, ENC, EtOH, and MeOH: Crystallization Index (Ci), Glass (Tg), Crystallization (Tc), and Degradation (Td).

DETAILED DESCRIPTION OF THE INVENTION

Figure 1:
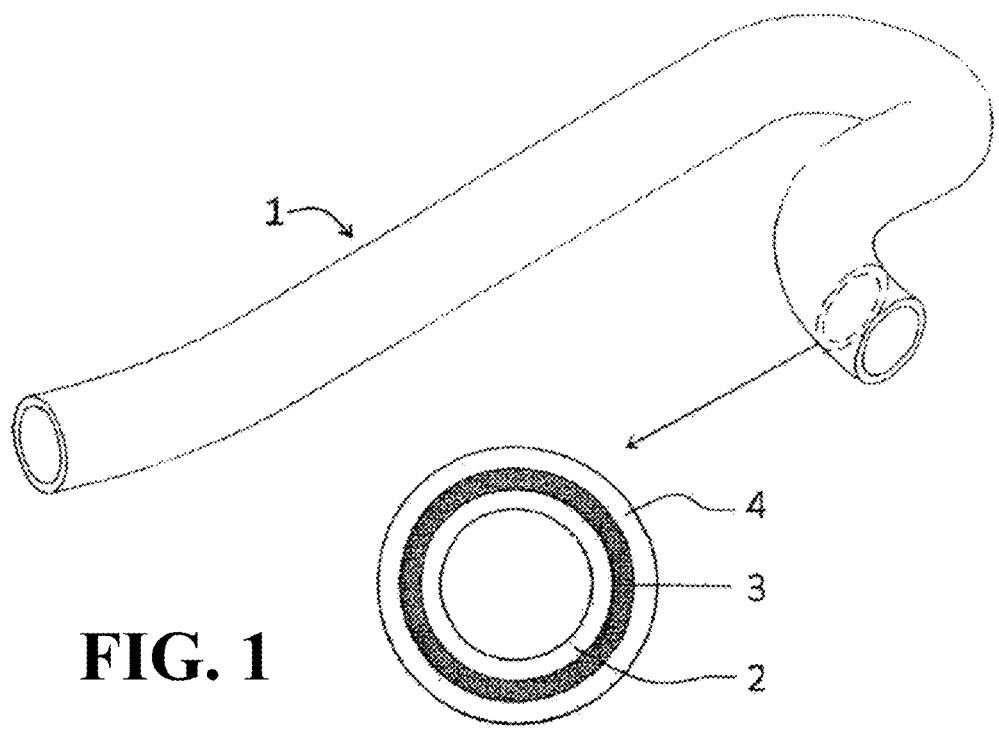
FIG. 1 shows a hybrid tubular scaffold 1 in fibroin and polyurethane.

The invention will now be described in detail with examples of embodiment and the help of the drawing in which FIGS. 1-4 are perspective/cross views.

FIG. 1 shows a hybrid tubular scaffold 1 in fibroin and polyurethane suitable for being used as a vascular prosthesis or as a vascular access, of internal diameter 7 mm and length 200 mm, with the following structural organization:
the first fibroin layer 2 has a thickness of 0.05 mm and a porosity of 60%;
the intermediate fibroin and polyurethane layer 3 has a thickness of 0.2 mm and a porosity of 40%;
the last fibroin layer 4 has a thickness of 0.04 mm and a porosity of 50%.

Figure 2:
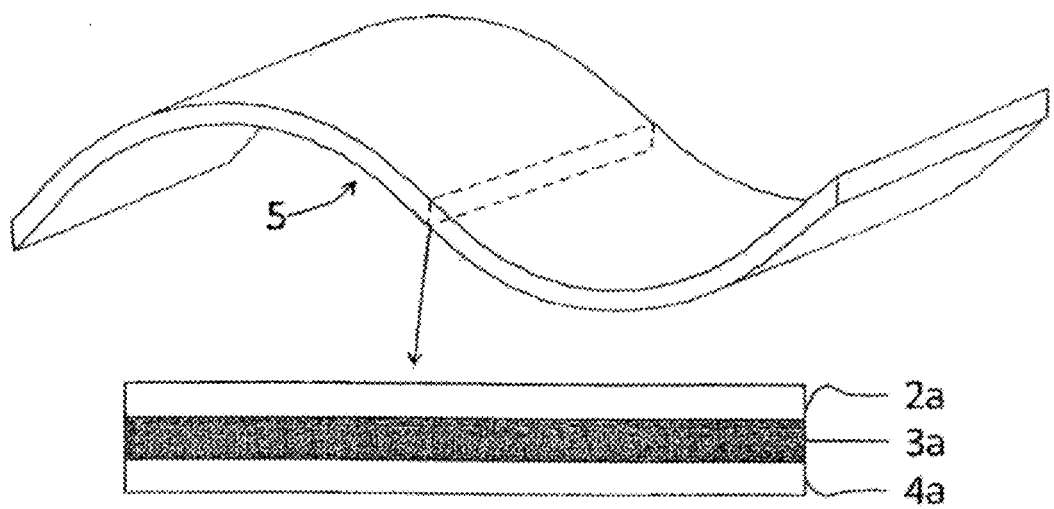
FIG. 2 shows a hybrid scaffold 5 in fibroin and polyurethane in the form of a shapeable lamella.

FIG. 2 shows a hybrid scaffold 5 in fibroin and polyurethane in the form of a shapeable lamella, 15 mm long and 5 mm wide, suitable for regenerating vascular tissues and in particular the myocardium, with the following structural organization,
the first fibroin layer 2a has a thickness of 0.3 mm and a porosity of 50%;
the fibroin and polyurethane intermediate layer 3a has a thickness of 0.2 mm and a porosity of 70%;
the last fibroin layer 4a has a thickness of 0.2 mm and a porosity of 40%.

Figure 3:
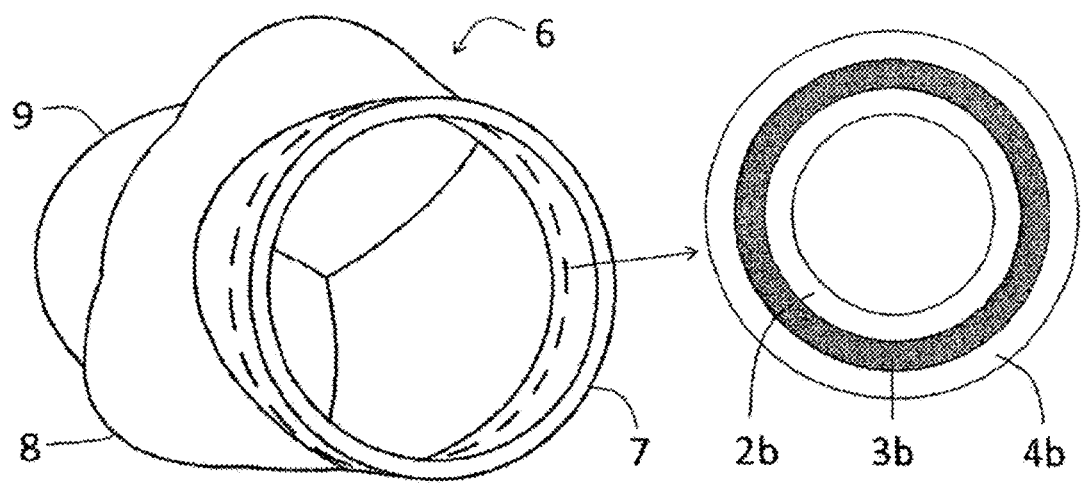
FIG. 3 shows a fibroin and polyurethane hybrid scaffolds 6 suitable for replacing an aortic valve.

FIG. 3 shows a fibroin and polyurethane hybrid scaffolds 6 suitable for replacing an aortic valve which comprises:
a proximal tubular part 7 suitable for connection to the ventricular myocardium, of a diameter and length congruent with those physiological in the implant anatomical site;

an intermediate part 8 of trilobate shape resembling the natural sinuses of Valsalva in the natural valve and hosting the three valve leaflets, or valve cusps;

a distal tubular part 9 suitable for the connection to the aorta, of diameter and length congruent with those physiological in the anatomical site of implantation, all three parts having in common the following structural organization:

the first fibroin layer 2b that has a thickness of 0.05 mm and a porosity of 60%, the intermediate fibroin and polyurethane layer 3b which has a thickness of 0.3 mm and a porosity of 40%;

the last fibroin layer 4b that has a thickness of 0.05 mm and a porosity of 60%.

Figure 4:
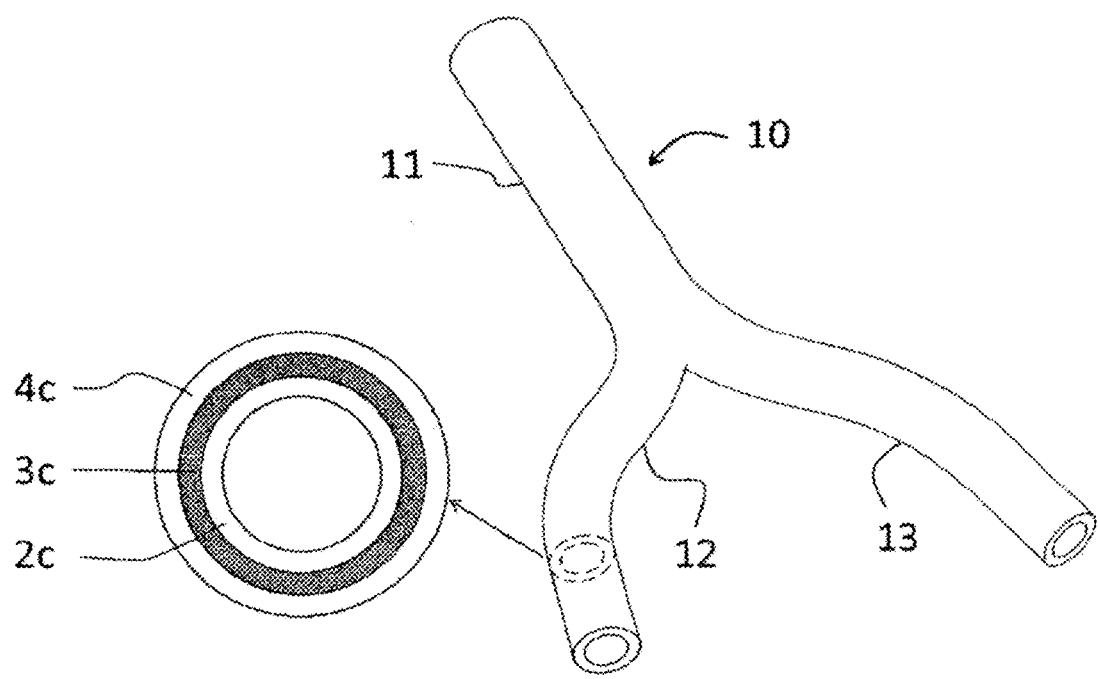
FIG. 4 shows a fibroin and polyurethane hybrid scaffolds 10 suitable for replacing the vascular tract called iliac bifurcation.
Figure 5:
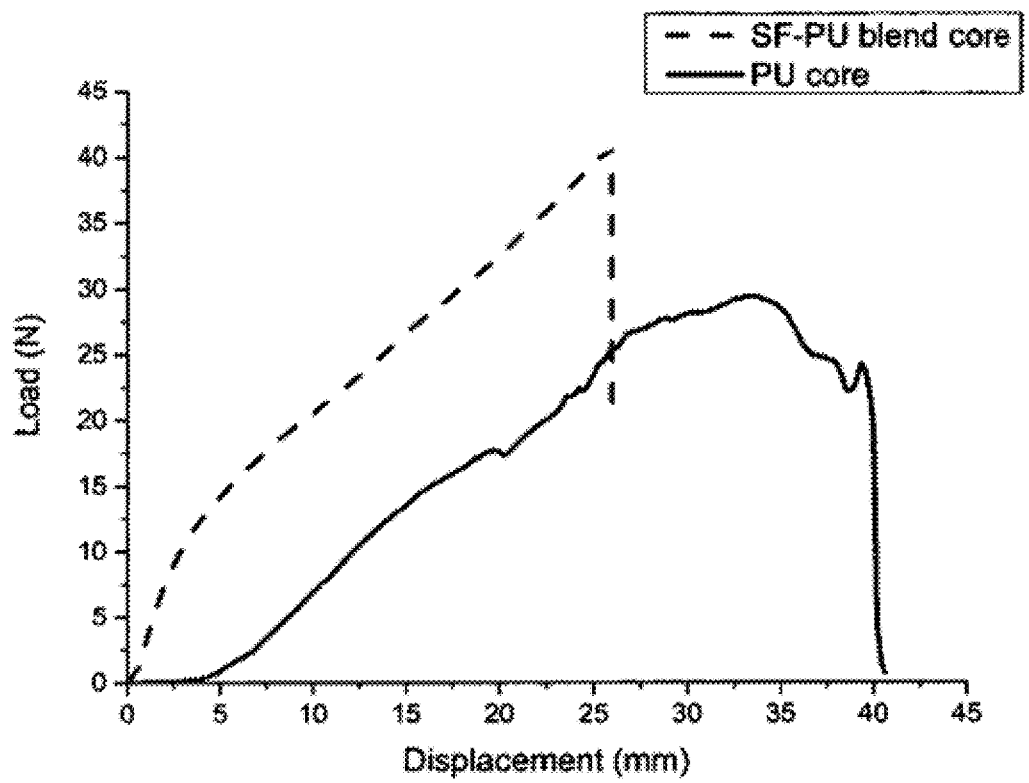
FIG. 5 is a graph of the characteristic "Load/Extension" curve of a sample made by electrospinning a layer of fibroin, electrospinning a subsequent layer of polyurethane and then electrospinning a second layer of fibroin ("PU core" plot). It is also shown the curve of a sample made by electrospinning a layer of silk fibroin, electrospinning a further layer of combined silk fibroin and polyurethane and then electrospinning a second layer of silk fibroin ("SF-PU blend core" plot).
Figure 6:
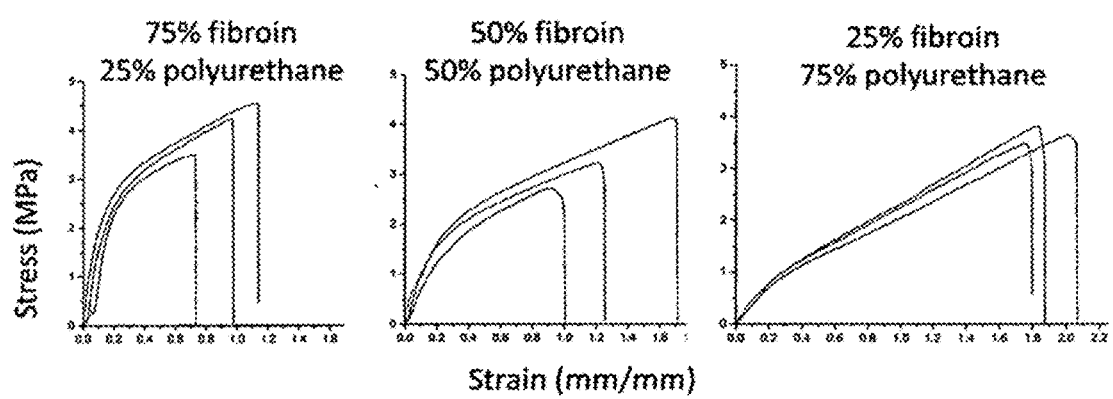
FIG. 6 depicts "Stress/Strain" graphs referred to electrospun meshes with intermediate layers of varied compositions (75% fibroin-25% polyurethane or 50% fibroin-50% polyurethane or 25% fibroin-75% polyurethane).
Figure 7:
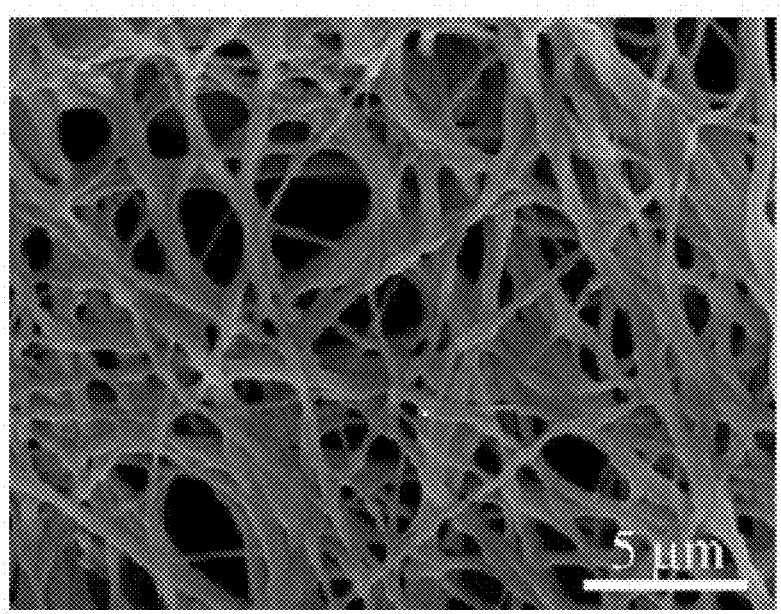
FIG. 7 shows meshes of an electrospun compound of silk fibroin and polyurethane using formic acid and dichloromethane (3:2).

FIG. 4 shows a fibroin and polyurethane hybrid scaffolds 10 which, suitable for replacing the vascular tract called iliac bifurcation, comprises:

a common tubular portion 11 suitable for the connection to the abdominal aorta of diameter and length congruent with those physiological of the anatomic implantation site;

two tubular sections 12, 13 arising from the common section 11, suitable for the connection to the common iliac arteries, of diameter and length congruent with those physiological in the anatomical implantation site, all three parts having in common the following structural organization:

the first fibroin layer 2c that has a thickness of 0.3 mm and a porosity of 50%, the intermediate fibroin and polyurethane layer 3b which has a thickness of 0.5 mm and a porosity of 40%;

the last fibroin layer 4b that has a thickness of 0.4 mm and a porosity of 60%.

In situ tissue engineering strategies, which rely on the patient's body as a bioreactor in alternative to in vitro culture before implantation, have been showing disruptive potential for clinical cardiovascular applications. [1-5] This approach, lately also called "endogenous tissue regeneration", proposes ready-to-use biodegradable scaffolds, with low manufacturing cost and lead time, designed to improve local tissue functionality while triggering regeneration. In this scenario, arteriovenous vascular grafts for hemodialysis represent a particularly interesting application of in situ tissue engineering, since these scaffolds could be used as "off-the-shelf" prostheses, offering the ultimate valuable and durable vascular access alternative for patients in the need for long-term hemodialysis, currently facing the choice between suboptimal alternatives, that is, native fistulae or fully synthetic grafts.[6] In fact, if properly designed, biodegradable arteriovenous vascular grafts would allow for immediate puncturing after implantation (early cannulation), thus enabling urgent hemodialysis, and would progressively evolve into a healthy native vascular tissue, granting superior patency on the long term. However, considering the acellular character of this approach, the successful outcome relies exclusively on the scaffold's material. This requires extra material engineering focus on the development of scaffolds that possess the desired predictable dynamic response at short-, medium- and long-term after implantation. In this direction, one promising strategy consists in combining a natural degradable material with a synthetic inert polymer, providing a "hybrid" alternative to the puristic in situ tissue engineering approach, which encompasses fully degradable scaffolds. Indeed, the implantation of a semi-degradable vascular graft would safeguard the mechanical functionality in the long-run, since the non-degradable material would remain inert in situ, while the natural material would be progressively replaced by newly developed tissue.

Silk fibroin and polyurethane are two possible candidates to pursue the "hybrid" goal. Silk fibroin has been approved by the US Food and Drug Administration (FDA) to be used in the form of surgical suture [7], it has demonstrated to induce a negligible inflammatory response [8, 9], to possess good biocompatibility properties in vitro and in vivo (rats) [10], and suitable hemocompatibility in a canine model [11]. Additionally, Zhang et al. demonstrated how ePTFE grafts (under commercialization for vascular access application), when coated internally with a layer of silk fibroin, increased their hemocompatibility in rabbits as a result of a natural development of a layer of endothelial cells, resembling the morphology of the intima layer in native blood vessels [12]. As regards polyurethanes, their overall biocompatibility properties are generally deemed to be good; however, as addressed in the following, the wide range of possible formulations might significantly influence their degree of biocompatibility [13]. The combination of polyurethane and silk fibroin has already been proposed in different formulations, morphologies, and ratios [14-34] with the aim to prepare scaffolds encompassing the bioactive compatibility and degradability of fibroin together with the elasticity and long-term biostability of polyurethanes. Studies that report the coupling of these two materials, however, have one or more critical drawbacks concerning industrial and clinical applicability. The majority of these works use solvents unaddressed or belonging to Class 1 (Solvents to be avoided) in the European Pharmacopoeia [14-20, 35] (for example, hexa-fluoro-isopropanol, also characterized by exorbitant costs, extreme volatility and difficult manageability), or polyurethanes that are degradable and/or not suitable for long-term medical application [18-28, 36], which would unlikely pass the exam of regulatory approval necessary for product certification and commercialization. Other works report the development of composite scaffolds [14, 15, 22, 29-32, 37], where fibroin and polyurethane are present in different, non-coalescent phases, and are therefore highly susceptible to separation and delamination [30], especially upon post-processing treatments (such as crystallization and sterilization, known to induce different volumetric changes in the natural and in the synthetic phases) or during in vivo remodeling. Both Bai et al. [27] and Liu et al. [26] report effective electrospinning of a polyurethane solution containing dispersed fibroin particles. This strategy potentially succeeds in gathering the elastic properties of polyurethane with the biocompatibility of silk fibroin; however, upon electrospinning, the non-dissolved fibroin particles are trapped inside polyurethane fibers, possibly hindering the fibers' mechanical resistance and reducing sur-face exposure suitable for cell attachment, therefore hampering the bioactive potential of fibroin. Iizuka et al. [34] developed an interesting method to blend fibroin and polyurethane using an organic solvent addressed by the European Pharmacopoeia. However, this strategy results in a blend with unknown concentrations of fibroin, possibly failing to achieve consistent results from different batches.

The present inventors have now found a hybrid semi-degradable material made of fibroin and polyurethane which is reported with the potential for in situ vascular tissue engineering applications, such as innovative arteriovenous vascular grafts for hemodialysis. Overcoming the limitations of the above cited studies, inventors have processed a blend of regenerated silk fibroin with a medical-grade [38], non-degradable polyurethane to prepare electrospun semi-degradable hybrid tubular scaffolds with an extracellular matrix-like morphology.

Several attempts made so far to combine silk fibroin and polyurethane, in order to prepare scaffolds encompassing the bioactivity of the former with the elasticity of the latter, suffer from critical drawbacks concerning industrial and clinical applicability (e.g., separation of phases upon processing, use of solvents unaddressed by the European Pharmacopoeia, and use of degradable polyurethanes). A successful blending of regenerated silk fibroin with a medical-grade, non-degradable polyurethane using formic acid and dichloromethane, and the manufacturing of hybrid, semi-degradable electrospun tubular meshes with different ratios of the two materials is reported in the present disclosure. Physicochemical analyses demonstrated the maintenance of the characteristic features of fibroin and polyurethane upon solubilization, blending, electrospinning, and postprocessing with ethanol or methanol. Envisioning their possible application as semidegradable substrates for hemodialysis arteriovenous grafts, tubular meshes were further characterized, showing submicrometric fibrous morphologies, tunable mechanical properties, permeability before and after puncture in the same order of magnitude as commercial grafts currently used in the clinics. Results demonstrate the potential of this material for the development of hybrid, new-generation vascular grafts with disruptive potential in the field of in situ tissue engineering.

In the following the terms "combination" and "mixture" may be both used to indicate a mixture of solvents.

According to this disclosure, it is provided a method of producing a solution of a compound consisting of silk fibroin and polyurethane dissolved in a combination of formic acid and dichloromethane, comprising the following steps: dissolving silk fibroin in formic acid, obtaining a first solution of silk fibroin in formic acid; dissolving polyurethane into a first combination of formic acid and dichloromethane, thus obtaining a second solution of polyurethane dissolved in formic acid and dichloromethane; mixing the first solution with the second solution together, obtaining a final solution of a compound of silk fibroin and polyurethane dissolved in a final combination of formic acid and dichloromethane.

According to an aspect of this disclosure, said first solution of silk fibroin in formic acid comprises 2 parts of formic acid with respect to the 5 parts of said final combination of formic acid and dichloromethane.

According to another aspect of this disclosure, said first combination of formic acid and dichloromethane for dissolving polyurethane comprises 2 parts of dichloromethane and 1 part of formic acid with respect to the 5 parts of said final combination of formic acid and dichloromethane.

According to an aspect of the present disclosure, said final solution of a compound of silk fibroin and polyurethane dissolved in a final combination of formic acid and dichloromethane comprises 3 parts of formic acid and 2 parts of dichloromethane.

According to another aspect of the present disclosure, said final solution of a compound of silk fibroin and polyurethane dissolved in a final combination of formic acid and dichloromethane comprises from 0.01% w/v to 98.01% w/v of silk fibroin and from 0.01% w/v to 98.01% w/v of polyurethane; preferably from 0.01% w/v to 9.9% w/v of silk fibroin and from 0.01% w/v to 9.9% w/v of polyurethane; and more preferably from 1.0% w/v to 3.0% w/v of silk fibroin and from 1.0% w/v to 3.0% w/v of polyurethane.

According to a particular aspect of this disclosure, the total concentration of silk fibroin and polyurethane in the final combination of formic acid and dichloromethane is 10% w/v or less, and preferably is 4.0% w/v.

According to an aspect of this disclosure, it is provided a method of preparing a solid layer of a compound made of silk fibroin and polyurethane, comprising the steps of: providing a solution of a compound made of silk fibroin and polyurethane dissolved in a final combination of formic acid and dichloromethane; depositing said compound made of silk fibroin and polyurethane in solid form onto a substrate throughout an electrospinning process of said solution, thus preparing a solid layer of said compound made of silk fibroin and polyurethane.

According to an aspect of this disclosure, it is provided a method of preparing a prosthesis made of a compound of silk fibroin and polyurethane, comprising the steps of: providing a solution of a compound made of silk fibroin and polyurethane dissolved in a final combination of formic acid and dichloromethane; depositing onto a substrate of silk fibroin, throughout an electrospinning process of the above said solution, a solid layer made of said compound of silk fibroin and polyurethane; preparing said prosthesis by coating said solid layer made of said compound of silk fibroin and polyurethane, with a coating layer made of silk fibroin.

According to an aspect of this disclosure, the solid layer of a compound made of silk fibroin and polyurethane prepared as described above is subjected to at least a washing/crystallization treatment with aqueous solutions of ethanol or methanol, preferably ethanol.

The present methods make therefore use of a novel sustainable solvent system for preparing a silk fibroin and polyurethane scaffold complying with the directions of the European Pharmacopoeia for the development of medical implants [35]. The effects produced on the raw materials by the solvent combination, blending, electrospinning, and post-processing treatments were investigated in the following experimental part in order to successfully maintain the intrinsic properties associated to fibroin and polyurethane. Moreover, the versatility of the proposed process was demonstrated, allowing for the manufacturing of meshes with tuneable concentrations of raw materials, which were characterized in terms of mechanical properties, morphology and permeability. Finally, in anticipation of their possible application as substrates for arteriovenous vascular grafts, the permeability of the meshes after puncture was assessed.

EXPERIMENTAL PART AND EXAMPLES

Materials and Methods

*Bombyx mori* cocoons were provided by the Council of Research and Experiments in Agriculture, Apiculture and Sericulture Unit (CREA-API; Padua, Italy). Poly-carbonateurethane (Carbothane® Aromatic, AC-4075A) pellets (PP, polyurethane pellets) were kindly supplied by Lubrizol (Wickliffe, Ohio, United States). All other chemical reagents were obtained from Carlo Erba (Cornaredo, Italy) unless otherwise mentioned.

Preparation of regenerated *Bombyx mori* silk fibroin
*Bombyx mori* cocoons were degummed at 120° C. for 15 min and washed to extract the sericin. Extracted fibroin fibers were solubilized in a 9.3 M lithium bromide solution (T=60±2_C, t=3 h under shaking) to obtain a final concentration of 10% w/v fibroin. The solution was then diluted with warm deionized water to obtain a 2% w/v fibroin concentration, filtered and dialyzed for three days using cellulose membrane tubing (Mw cut-off=14,000 Da) to eliminate lithium bromide salts. Finally, fibroin films (FF) were prepared by solvent casting. Table I contains a complete list of the samples and acronyms used in this disclosure.

evaluated by processing the following different blend solutions: 1% w/v fibroin and 3% w/v polyurethane (SF25PU75), 2% w/v fibroin and 2% w/v polyurethane (SF50PU50), and 3% w/v fibroin and 1% w/v polyurethane

TABLE I

Processing Parameters Used to Prepare Samples PP, PFS, FF, FFS, BFS, ENC, EtOH, and MeOH, Regarding Concentration of Raw Materials and Organic Solvents Used on Solution Preparation, Electrospinning Parameters and Post-treatment Times Employed: SF, silk fibroin; PU, polyurethane; FA, formic acid; DCM, dichloromethane; t, processing time; ΔV, electrospinning voltage; d, distance between spinneret and collector; Q, flow rate of electrospinning solution; EtOH*, ethanol-based post-treatment; MeOH*, methanol-based post-treatment.

| Sample Acronym | Sample Long Name | % SF [w/v] | % PU [w/v] | FA:DCM [v:v] | t [h] | ΔV [kv] | d [cm] | Q [mL/h] | EtOH* [hh:mm] | MeOH* [hh:mm] |
| --- | --- | --- | --- | --- | --- | --- | --- | --- | --- | --- |
| PP | Polyurethane pellets | — | 100% | — | — | — | — | — | — | — |
| PFS | Solvent cast polyurethane films | — | 2% | 3:2 | O/N | — | — | — | — | — |
| FF | Aqueous fibroin films | 100% | — | — | — | — | — | — | — | — |
| FFS | Solvent cast fibroin films | 2% | — | 3:2 | O/N | — | — | — | — | — |
| BFS | Solvent cast blend films | 2% | 2% | 3:2 | O/N | — | — | — | — | — |
| ENC | Electrospun hybrid mesh noncrystalilzed | 2% | 2% | 3:2 | 8 | 17 | 19 | 2:5 | — | — |
| EtOH | Electrospun hybrid mesh crystallized with ethanol | 2% | 2% | 3:2 | 8 | 17 | 19 | 2.5 | 20:00 | — |
| MeOH | Electrospun hybrid mesh crystallized with methanol | 2% | 2% | 3:2 | 8 | 17 | 19 | 2:5 | — | 00:10 |

Blending Silk Fibroin and Polyurethane

The fibroin/polyurethane blend solution was prepared by first dissolving each raw material separately and later joining them into one solution. Briefly, fibroin films were cut into small pieces and dissolved (T=room temperature (RT), t=1 h, 150 rpm) in formic acid (FA). In parallel, polyurethane was dissolved (T=RT, t=1 h, 250 rpm) in a 1:2 ratio of FA and dichloromethane (DCM), respectively. The polyurethane solution was then progressively transferred into the fibroin solution and further stirred (T=RT, t=15 min, 150 rpm) to achieve a blend solution with a final concentration of 2% w/v of each material within a 3:2 ratio of FA and DCM, respectively. The blend solution was either used to produce blend films by solvent casting (BFS), to evaluate the blending effect on the raw materials, or to prepare blend electrospun samples (ENC, electrospun non-crystallized), using the parameters described in Table I, to assess potential damages induced by electrospinning. Moreover, in order to evaluate the effect of solvents on the single raw materials, control films of pure fibroin (FFS) and pure polyurethane (PFS) were prepared by casting solutions prepared as described above for the blend, but skipping the addition of polyurethane and fibroin, respectively. Finally, with the aim of developing a more industrially sustainable crystallization treatment for silk fibroin, as an alternative to the common practice with methanol, an ethanol-based process was tested. Ethanol-crystallized electrospun blend samples (EtOH) were prepared by posttreating ENC samples in a descending series of ethanol/demineralized water solutions, upon stirring at 150 rpm: 50% v/v (1 h), 50% v/v (15 h), 25% v/v (1 h), 25% v/v (1 h), 100% H2O (1 h). EtOH samples were used to evaluate the post-treatment effect on the raw materials, the development of ß-sheet conformations and the removal efficiency of solvents. As a control, methanol-crystallized electrospun blend samples (MeOH) were prepared by dipping ENC samples in a solution of 80% v/v methanol/demineralized water for 10 min.

Electrospinning of Hybrid Tubular Meshes

The feasibility of manufacturing hybrid electrospun tubular meshes with tuneable fibroin/polyurethane ratios was evaluated by processing the following different blend solutions: (SF75PU25). The samples were electrospun using the same electrospinning parameters employed on the preparation of samples ENC, EtOH and MeOH (Table I). Briefly, the blend solution was loaded into a solvent resistant syringe controlled by a pump delivering a constant flow rate (2.5 mL/h) to a spinneret (+17 kV), which was moving (velocity=5 mm/s; path length=20 cm) in parallel to a rotating (1000 rpm) metal rod collector (diameter=8 mm; L=32 cm), covered with aluminum foil, over a total period of 8 hours for each formulation. Electrospun hybrid tubular meshes were post-treated using the same crystallization protocol described above to prepare EtOH samples.

Characterization

Physicochemical properties. Physicochemical analyses were made on samples PP, PFS, FF, FFS, BFS, ENC, EtOH and MeOH, by Fourier transform infrared (FTIR) spectroscopy (N=3) and differential scanning calorimetry (DSC), to evaluate the effects of solvent mixture, blending, electrospinning, and post-treatment on the raw materials. FTIR was performed using an attenuated total reflectance spectrometer, acquiring the spectra between the wavelengths of 4000 and 375 cm-1, with a resolution of 1.42 cm-1. The absorption peak of amide I (1703-1605 cm-1) was deconvoluted using OriginPro (version 9.1; OriginLab Corporation, United States) by adapting a protocol previously reported [39]. For the quantification of the samples' crystallinity index (Ci), the different contributions were fit using Gaussian peaks. In the samples with polyurethane and silk blends (BFS, ENC, EtOH and MeOH), the polyurethane contribution was fit together with the silk.

DSC measurements were acquired with a DSC Q200 (TA Instruments; United States) during three heating cycles alternated with periods of cooling and temperature maintenance. The second derivative of heat flow during the heating ramp was used to find the glass (Tg), crystallization (Tc) and degradation (Td) temperatures.

Structure and Morphology

The fibrous morphology of above identified samples SF25PU75, SF50PU50, and SF75PU25 was analyzed by scanning electron microscopy (SEM). Briefly, each sample was coated with a layer of gold and further observed under a SEM equipment (MIRA3; Tescan, Czech Republic) operating at 10 kV. The diameter of fibers at ×5000 magnification was measured using ImageJ software (ImageJ 1.50i; National Institutes of Health, United States) for at least 249 fibers.

Mechanical Properties

Uniaxial tensile tests were performed on samples SF25PU75, SF50PU50, and SF75PU25, after cutting dog-bone shaped specimens in the longitudinal direction from opened and flattened electrospun tubular matrices. Tensile properties were measured at room temperature (RT), after hydrating the samples in distilled water for 10 min, using a tensile testing system (LF Plus; Lloyd Instruments, United Kingdom), with a load cell of 100 N, at 100 mm·min-1 until break. Strain was calculated in relation to the 24 mm gauge length and stress was calculated in relation to a crossectional area with 5 mm width and the average thickness measured using a micrometer before starting the test (293-805; Mitutoyo, Japan). Young's modulus was retrieved by doing a linear regression of the elastic domain in each sample. Maximum elongation at break, stress at break and Young's modulus were averaged from 3 replicates and corresponding standard deviations were calculated for each condition. Dog-bone specimens derived from a commercial ePTFE (expanded polytetrafluoroethylene) graft were similarly tested as a term of comparison (n=2).

Permeability Before and after Puncture

Water permeability was measured on above identified samples SF25PU75, SF50PU50, SF75PU25 and on commercial arteriovenous vascular grafts: a polyurethane electrospun graft (ES PU), an ePTFE prosthesis graft, and a three-layered arteriovenous vascular graft containing ePTFE (3-layer ePTFE). Briefly, a 14 mm diameter circular punch was used to cut samples with consistent size, after longitudinally opening and flattening the electrospun tubular matrices (N>3 for SF25PU75, SF50PU50, SF75PU25, N=1 for commercial grafts). Each sample was hydrated (demineralized water; t>10 min) and assembled in a cylindrical chamber held between two silicon O-rings that allowed a circular perfused area with a diameter of 11 mm. Each test was conducted at a constant pressure of 120 mmHg for 6 hours. The volume of diffused demineralized water was measured at each hour. The flow rate was further used to calculate the permeability k using Darcy equation (Eq. 1):

$$Q = \frac{k \cdot A \cdot \Delta P}{\mu \cdot L} \quad (1)$$

In Eq. (1), Q is the flow rate, A is the cross-sectional perfused area, ΔP is the relative pressure of the medium at the sample location, μ is the viscosity of the medium used, and L is the thickness of the sample. Following these tests, samples were punctured under 120 mmHg with a 15 G hemodialysis needle. The volume of water permeated through the sample was collected for 1 min, after retrieval of the needle. The measured flow rate was used to calculate the Darcy permeability after puncture.

Statistical Analysis

One-way ANOVA was used to perform the statistical analysis where appropriate, considering significance at p<0.05.

Results

Physicochemical Properties

FIG. 8(A) shows the full infrared absorbance spectra of samples PP, PFS, FF, FFS, BFS, ENC, EtOH, and MeOH. By comparing sample PP with PFS, and FF with FFS, it is possible to conclude that both polyurethane and fibroin retain their overall characteristic features after dissolution within the proposed solvent system. In fact, the spectrum of PP is comparable to the PFS aside from a small decrease in absorbance on the two major peaks, at 1740-1735 cm-1 (carbonyl, C=O, 1750-1700 cm-1) and 1245-1240 cm-1 (ester, —C—O—C—, 1260-1230 cm-1), that could indicate a mild increase in hardness [41]. As to fibroin, typical absorbance bands of amides I (C=O stretching vibration), II (C—N stretching and N—H distortion vibration) and III (C—N stretching and N—H deformation vibration) [27] were observed at peaks 1640, 1514 and 1234 cm-1, respectively, on both FF and FFS, with the latter also retaining all the other nine original peaks [FIG. 8(B)]. However, FFS showed a shift in the amides I, II, and III when compared to sample FF, with the first two shifting toward high wavelengths, and the latter significantly increasing the 1260 cm-1 shoulder. This indicates that the used solvent mixture induces a crystallization effect on fibroin, with the development of ß-sheet molecular conformations; the effect is observed, as well, when fibroin is blended with polyurethane in sample BFS. Besides that, the analysis of sample BFS confirms that also after blending fibroin and polyurethane maintain their characteristic features, since all peaks detected independently on FFS and PFS were observed in the BFS spectrum, as main peaks or subpeaks. Interestingly, ENC samples, that is, electrospun noncrystallized meshes manufactured from the same solution as BFS (cast) samples, did not show a peak shifting in amides I, II, and III as observed in samples FFS and BFS, hinting at the absence of solvent-related crystallization effect upon electro-spinning. A possible reason might be the difference in exposure time of fibroin to the solvent mixture, since solvent casting occurred overnight, during several hours, while each electrospinning session (that is, contact of fibroin with solvents within the solution) took only a couple of hours. Apart from this, the spectrum of ENC was an overlap of FF together with PP or PFS, allowing to conclude that the proposed electrospinning protocol does not induce significant changes in the raw materials. As regards post-processing treatments, EtOH and MeOH spectra were identical, both showing a crystallization effect in the amide I region in comparison with non-treated electrospun samples (ENC).

Since PP and PFS showed no absorbance on the amide I region, a detailed analysis of the ß-sheet contribution was conducted in this region [FIG. 8(C), areas highlighted in grey]. Deconvolution of the absorbance peak of amide I, in all samples, enabled the quantification of the total ß-sheet contribution (crystallization index, Ci, Table II), that resulted 31.4%±3.3%, 39.4%±2.1%, 37.9%±0.5%, 28.4%±0.8%, 40.5%±0.9%, and 39.6%±1.1% for FF, FFS, BFS, ENC, EtOH and MeOH, respectively, confirming the above reported conclusions regarding the crystallization effect of solvents, electrospinning, ethanol and methanol treatments. Further deconvolution analysis revealed that the crystallization effect caused by the solvent mixture (FFS, BFS) was related to the formation of weak ß-sheets or aggregated ß-strands observed on sub-peaks 1703-1697 cm-1 and 1621-1616 cm-1. In fact, inter- and intramolecular strong ß-sheets typically observed in two peaks within the 1637-1622 cm-1 region [39] were not significant on FFS or BFS versus FF or ENC samples, but were indeed pronounced on samples EtOH and MeOH, revealing a high content of strong ß-sheets induced by both crystallization treatments.

Figure 9:
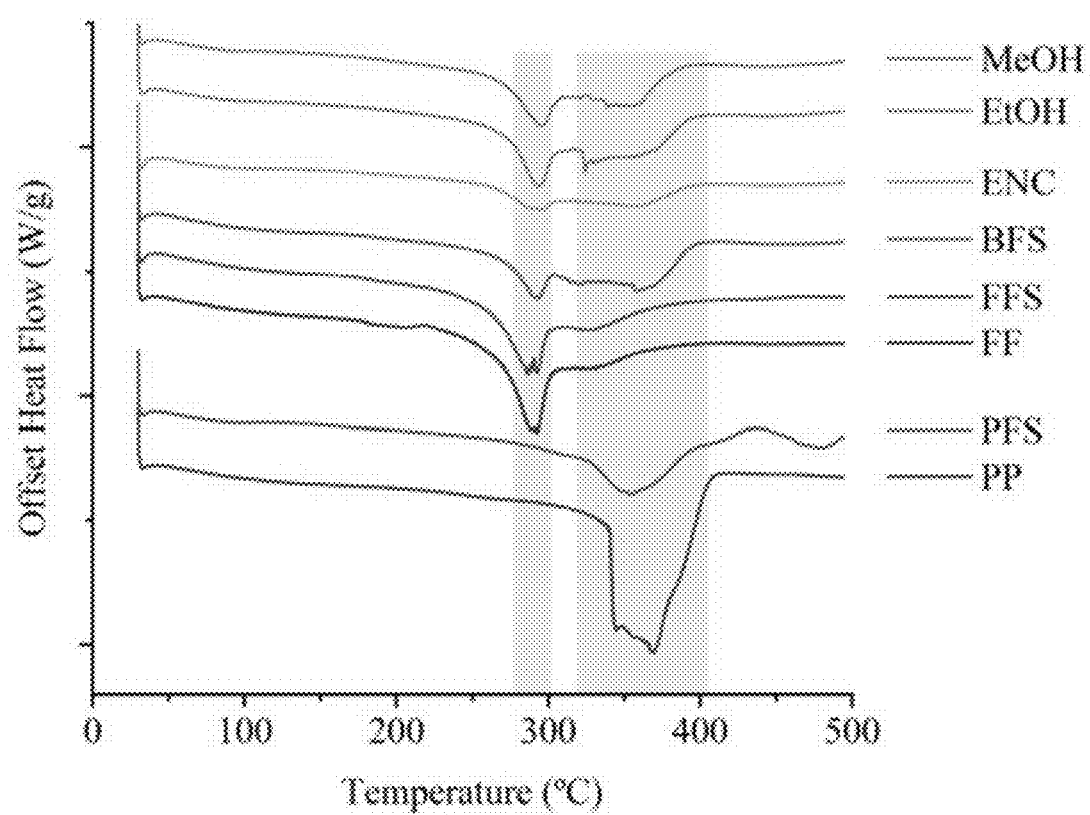
FIG. 9 shows DSC analysis plots of samples PP, PFS, FF, FFS, BFS, ENC, EtOH, and MeOH showing the final heating phase. Highlighted in gray is the degradation transitions ascribed to fibroin (around 270-300° C.) and polyurethane (approximately between 320 and 400° C.).

FIG. 9 represents the heat flow during the heating ramp of DSC performed on samples PP, PFS, FF, FFS, BFS, ENC, EtOH, and MeOH, allowing the extrapolation of the characteristic transitions of each sample (glass transition temperature, Tg, crystallization temperature, Tc, and degradation temperature Td, summarized in Table II, see FIG. 13).

Table II provides the results of the physicochemical analysis of Samples PP, PFS, FF, FFS, BFS, ENC, EtOH, and MeOH: Crystallization Index (Ci), Glass (Tg), Crystallization (Tc), and Degradation (Td) Temperatures: Degradation temperatures ascribed to fibroin (1°) and polyurethane (2°) are shown separately for samples containing both materials (BFS, ENC, EtOH, and MeOH). The degradation transitions ascribed to fibroin (around 270-300° C.) and polyurethane (approximately between 320 and 400° C.), again confirmed the persistence of both materials in blended samples. More in details, the conclusions drawn above as regards the crystallization effect of solvents, electrospinning and post-treatments are corroborated by the comparison of the crystallization temperatures of FFS (230° C.), BFS (226° C.), ENC (217° C.), EtOH (223° C.), and MeOH (227° C.) as compared to FF (217° C.) samples.

Structure and Morphology

Electrospun hybrid tubular meshes appeared as white hollow cylinders, with an overall length of about 22 cm [FIG. 10(A)] and inner diameter of approximately 7 mm. SEM images revealed the presence of a fibrous morphology in all samples SF25PU75 [FIG. 10(B)], SF50PU50 [FIG. 10(C)] and SF75PU25 [FIG. 10(D)]. There was a reduced presence of beads in SF50PU50 confirming suitable electrospinning parameters for this blend ratio. Diameter analysis revealed a distribution within an overall range of 0.050-2.150 μm.

A higher fiber diameter polydispersity was detected on SF25PU75 [FIG. 10(E)] and SF75PU25 [FIG. 10(G)] as compared to SF50PU50 [FIG. 10(F)], which showed a more condensed range of fiber diameter between 0.050-0.800 μm, with an average of 0.316±0.121 μm, confirming optimal fabrication parameters for this formulation. The main morphological characteristics of the electrospun hybrid meshes are summarized in Table III.

TABLE III

Quantitative Characteristics of all Formulations of Electrospun Hybrid Meshes: SF25PU75, SF50PU50, and SF75PU25, Regarding Wall Thickness, Fiber Diameter, Mechanical Properties, and Permeability (k) Before and After Puncture

|  | SF25PU75 | SF50PU50 | SF75PU25 |
| --- | --- | --- | --- |
| Wall thickness (mm) | 130 ± 26 | 164 ± 22 | 182 ± 21 |
| $\Phi_{fiber}$ (mm) | 0.348 ± 0.329 | 0.316 ± 0.121 | 0.559 ± 0.203 |
| E (MPa) | 3.96 ± 0.37 | 10.60 ± 1.52 | 23.50 ± 1.89 |
| Elongation at break (%) | 173 ± 24 | 127 ± 31 | 93 ± 17 |
| Stress at break (MPa) | 3.65 ± 0.13 | 3.35 ± 0."58 | 4.09 ± 0.44 |
| k (m$^2$) before puncture | 2.93 × 10$^{-17}$ ± 1.75 × 10$^{-17}$ | 9.75 × 10$^{-18}$ ± 1.13 × 10$^{-18}$ | 4.19 × 10$^{-17}$ ± 1.26 × 10$^{-17}$ |
| k (m$^2$) after puncture | 1.85 × 10$^{-13}$ ± 1.55 × 10$^{-14}$ | 1.96 × 10$^{-13}$ ± 5.79 × 10$^{-14}$ | 1.18 × 10$^{-13}$ ± 2.89 × 10$^{-14}$ |

Mechanical Properties

Figure 11:
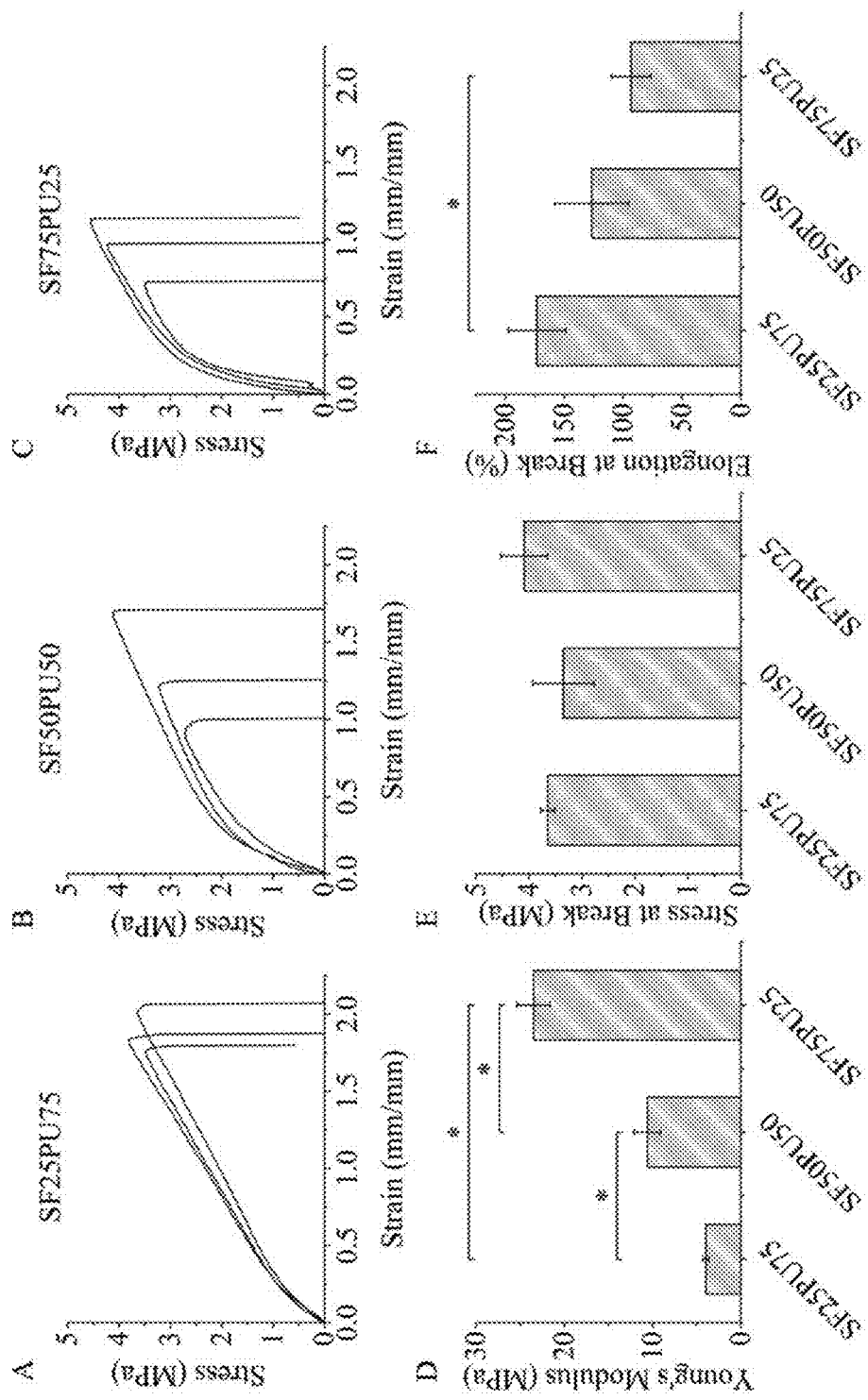
FIG. 11 shows stress-strain plots of uniaxial tensile tests performed on samples SF25PU75 (A), SF50PU50 (B), and SF75PU25 (C) allowing for the calculation of Young's modulus (D), stress at break (E), and elongation at break (F). Results are expressed as average ±standard deviation, n=3. *Significance was considered at p<0.05.

FIG. 11 shows the stress-strain plots of the axial tensile tests of SF25PU75 [FIG. 11(A)], SF50PU50 [FIG. 11(B)], and SF75PU25 [FIG. 11(C)] dog-bone specimens. Below, histograms show average values and standard deviations (N=3) of the Young's modulus [FIG. 11(D)], stress at break [FIG. 11(E)] and elongation at break [FIG. 11(F)] of the three blend formulations. A statistically significant increase in Young's modulus is observed in formulations with increasing fibroin content, from 3.96±0.37 MPa for SF25PU75, to 10.60±1.52 MPa for SF50PU50 and 23.50±1.89 MPa for SF75PU25, while an increasing elongation at break is seen in samples with increasing polyurethane content (173±24% for SF25PU75, 127±31% for SF50PU50 and 93±17% for SF75PU25). Interestingly, stress at break revealed no significant difference between different blend ratios, with a mean value of 3.70±0.30 MPa. Table III also summarizes the main mechanical properties of the electrospun hybrid meshes. ePTFE samples showed an average Young's modulus of 34.66 MPa, elongation at break of 87.77%, and stress at break of 18.73 MPa.

Permeability

Figure 12:
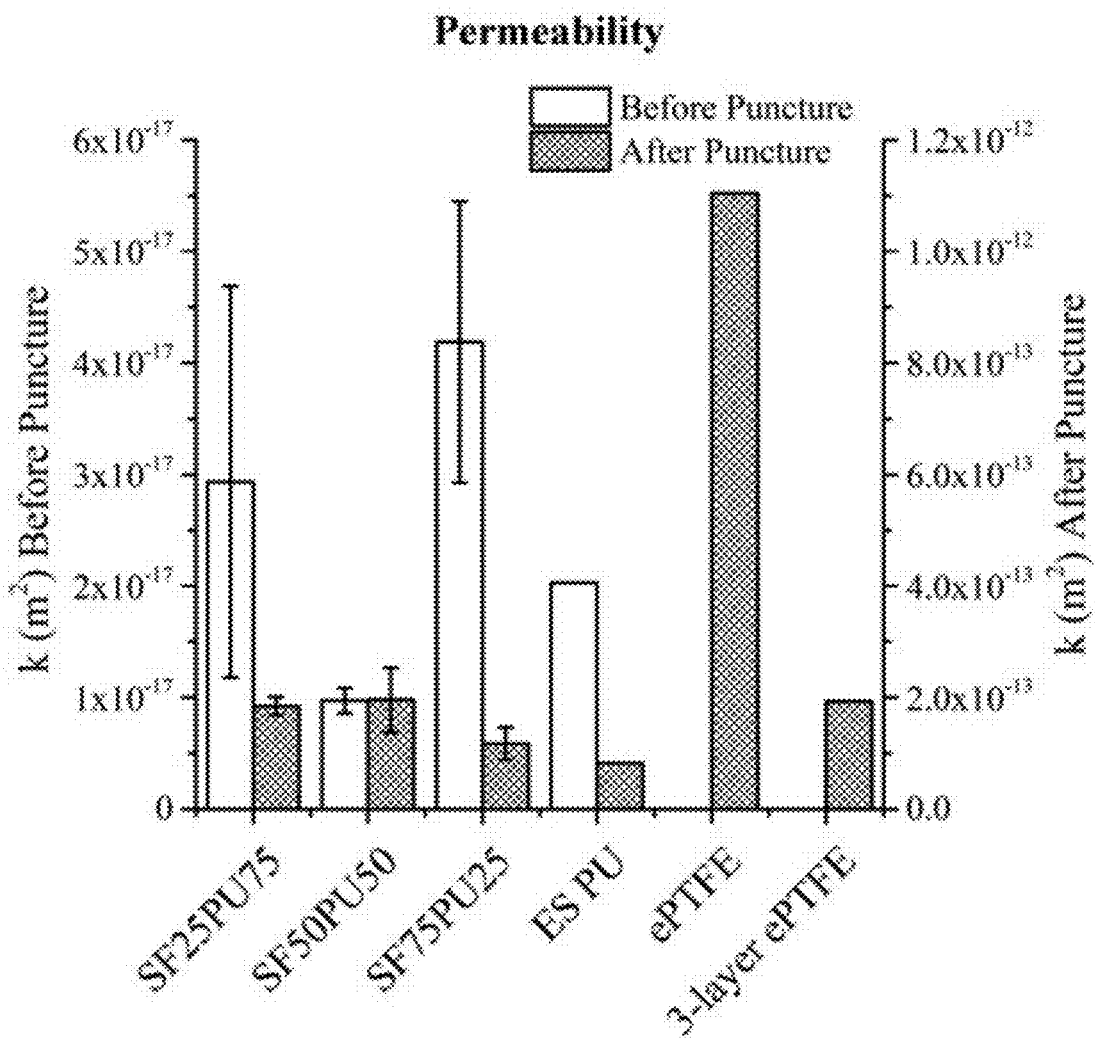
FIG. 12 shows Darcy permeability (k) of samples SF25PU75, SF50PU50, and SF75PU25 as compared to commercially available grafts (ES PU, polyurethane electrospun graft; ePTFE, expanded polytetrafluoroethylene graft; 3-layer ePTFE, three-layered graft containing ePTFE), before (white columns) and after (criss-cross columns) puncturing with a needle (15 G) typically used in hemodialysis procedure (N=3 for SF25PU75, SF50PU50, SF75PU25, N=1 for commercial grafts). ES PU and 3-layer ePTFE are deemed to be grafts capable of self-sealing after retrieval of the needle (i.e., low permeability after puncture).

The Darcy permeability values of samples SF25PU75, SF50PU50, and SF75PU25 (FIG. 12) were 2.93×10$^{-17}$± 1.75×10$^{-17}$ m$^2$, 9.75×10$^{-18}$±1.13×10$^{-18}$, and 4.19×10$^{-17}$± 1.26×10$^{-17}$ m$^2$, respectively (Table III). These were in the same order of magnitude of commercially available electrospun polyurethane vascular grafts (ES PU), with a permeability of 2.03×10$^{-17}$ m$^2$. The higher standard deviation in permeability of samples SF25PU75 and SF75PU25 was in line with the frequency in the presence of beads within the same samples, that would require optimization of processing parameters for the corresponding formulations. Samples ePTFE and 3-layer ePTFE were impermeable at 120 mmHg.

Permeability after Puncture

After puncturing the electrospun meshes with a standard hemodialysis needle (15 G), the permeability increased by four orders of magnitude in samples SF25PU75, SF50PU50, and SF75PU25 (FIG. 12) to 1.85×10$^{-13}$±1.55×10$^{-14}$ m$^2$, 1.96×10$^{-13}$±5.79×10$^{-14}$ m$^2$, and 1.18×10$^{13}$±2.89×10$^{-14}$ m$^2$ (Table III), respectively, following the same trend of the commercially available electrospun vascular grafts, of 8.22× 10$^{-14}$ m$^2$. The gold standard arteriovenous vascular graft composed of an elastomer and ePTFE (3-layer ePTFE), deemed to be capable of self-sealing after puncture, also had permeability of 1.93×10$^{-13}$ m$^2$. In contrast, the traditional ePTFE graft was completely outperformed, showing a permeability after puncture of 1.10×10$^{-12}$ m$^2$.

Discussion of the Experimental Results

Despite the increasing interest lately raised by the so-called "in situ approach" to tissue engineering [1-5], the industrial practicability and the clinical applicability of this strategy, traditionally relying on the use of fully degradable scaffolds, is far from being a reality. The scarcely controllable degradation rate of these scaffolds, which would likely be highly site- and patient-dependent, will make their regulatory approval and clinical transferability, at the very least, complex and adventurous. This is especially true for those applications (for example, in the cardiovascular district) where a mismatch between the degradation rate of the scaffold and the production of new tissue by the host could dramatically result in the implant's failure, and ultimately in the patient loss. To overcome this limitation, a "hybrid" approach to in situ tissue engineering could be adopted, based on the use of semi-degradable scaffolds combining a natural, biodegradable material—typically showing superior bioactivity and biocompatibility—with a synthetic, non-degradable one, granting a permanent backbone with adjustable and stable mechanical properties. This type of scaffold could be particularly beneficial in the field of vascular accesses (that is, the arteriovenous shunts that allow for hemodialysis), where there is an urgent, unmet, global need for grafts that show suitable mechanical properties for early cannulation (that is, that can be punctured immediately after implantation), as well as the capability to integrate and remodel in the long-term, which is known to be the key to a positive clinical outcome [6]. Based on this rationale, inventors report the successful blending of regenerated silk fibroin with an aromatic, medical grade, highly biocompatible poly-carbonate-urethane [38] by using a solvent mixture of formic acid and dichloromethane, and the manufacture of electrospun hybrid tubular meshes, whose properties can be tuned according to the respective ratios of the raw materials in the blend. Indeed, our approach overcomes the limitations of several studies, already cited in the introductory section in this work, coupling fibroin and polyurethane in an attempt at combining the properties of natural and synthetic materials. In particular, making use of solvents addressed by the European Pharmacopeia [35], and blending fibroin together with a non-degradable polyurethane, represents a potential industrially-sustainable solution to regulatory hurdles (related to residual solvents and degradable polyurethanes) and technical issues (the separation of fibroin and polyurethane during processing).

As shown above, fibroin and polyurethane were processed through several steps, namely: dissolution, blending, electrospinning and post-treatment, and none of these steps have altered the materials' intrinsic properties, as shown above in the investigation of the effects of each processing step on the raw materials (used in a 1:1 ratio in the blend formulations, Table I).

Figure 8:
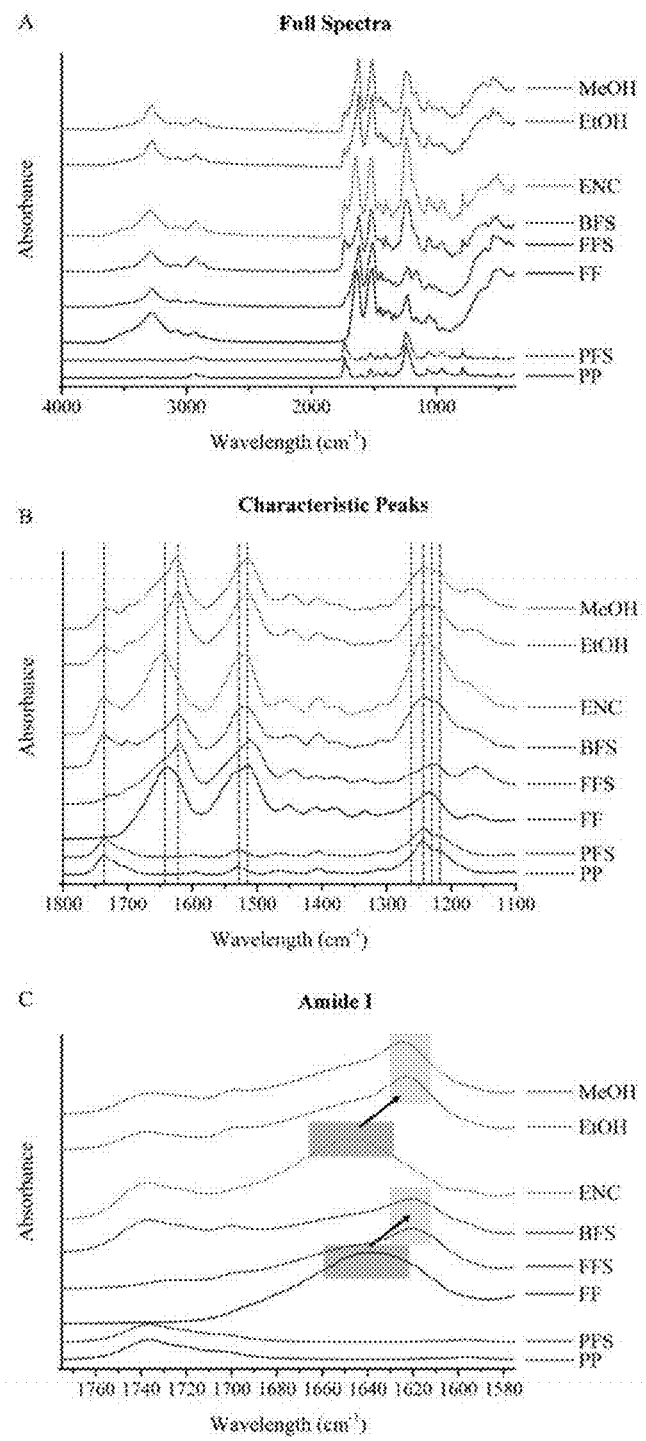
FIG. 8 shows FTIR spectra of samples PP (polyurethane pellets), PFS (Solvent cast Polyurethane Films), FF (Aqueous Fibroin Films), FFS (Solvent cast Fibroin Films), BFS (Solvent cast Blend Films), ENC (Electrospun hybrid mesh Non-Crystallized), EtOH (Electrospun hybrid mesh crystallized with ethanol), and MeOH (Electrospun hybrid mesh crystallized with methanol), (A) at full scale, (B) between 1800 and 1100 $cm^{-1}$, and (C) at the amide I region. Dashed lines represent the characteristic wavelengths of polyurethane (at 1740-1735 and 1245-1240 $cm^{-1}$) and fibroin (amides I-III around 1640, 1514, and 1234 $cm^{-1}$). Regions highlighted in gray allow to detect the crystallization effect of solvents (FFS and BFS vs. FF), electrospinning (ENC vs. BFS), and ethanol- and methanol treatments (EtOH and MeOH vs. ENC) on fibroin ß-sheet arrangements.

Moreover, physicochemical analyses (FIGS. 8 and 9; Table II) demonstrated that both materials, silk fibroin and polyurethane, retained their characteristic features after dissolution within the proposed solvent system, and allowed to rule out possible denaturation, degradation, or chemical reactions between them in the blend; also, electrospun blend samples did not show significant effects on the raw materials if compared with cast blend films. A particular attention was dedicated to the analysis of the effect of the different processing steps on the crystallization of fibroin. The degree of crystallinity of silk fibroin, which is related to its molecular conformations (fraction of ß-sheets in relation to a-helix and random turns [39]) is in fact known to significantly affect the material's characteristics, for example, in terms of solubility, mechanical properties, and degradation rate [41].

Indeed, regenerated fibroin can be water soluble and mechanically unstable in the amorphous state (higher a-helix fraction) or insoluble and mechanically stable in the crystalline state (predominant ß-sheet fraction) [42, 43]. In the perspective of an industrially sustainable scaffold manufacturing process, the characterization, and possibly the control of the degree of crystallization of fibroin, is imperative to ensure reproducibility of the process and repeatability of the product's features (for example, shelf life, in vivo degradation rate, stiffness). To this purpose, deconvolution of the amide I peak allowed to calculate the crystallization index (Ci) of fibroin-containing samples. As regards the post-processing treatments, it was demonstrated that the proposed ethanol-based protocol induces a similar crystallization effect as compared to the traditional methanol-based one (more expensive and hazardous). Interestingly, both EtOH and MeOH samples revealed a higher glass transition temperature of 202° C. as compared to the 181.3-182.6° C. recorded in all other samples. Hu et al. also analyzed fibroin samples crystallized with methanol, by DSC, and likewise observed a glass transition temperature of 202° C., indicating that this effect is caused by ß-sheet crystallization [39]. However, the same was not observed in samples FFS an BFS, where the glass transition temperature remained equal to FF samples, but both the crystallization temperature and index were in line with EtOH and MeOH samples.

Deconvolution of the FTIR absorbance of amide I peak, in all samples, revealed that the crystallization effect caused by the overnight exposure to the solvent mixture (FFS, BFS) was related to the formation of weak ß-sheets or aggregated ß-strands observed on subpeaks 1703-1697 cm-1 and 1621-1616 cm-1. In fact, inter- and intramolecular strong ß-sheets typically observed in two peaks at the 1637-1622 cm-1 region [39] were not significant on FFS or BFS versus FF samples, but were indeed pronounced on samples EtOH and MeOH, revealing a high content of strong ß-sheets induced by both crystallization treatments. Upon observing that the effects of ethanol and methanol produced the same type and degree of crystallization, the average spectrum of EtOH samples was subtracted from the MeOH average, to evaluate what remained: interestingly, three major peaks were observed at 1740-1720 $cm^{-1}$ and 1260-1230 $cm^{-1}$, which coincide with characteristic peaks of formic acid and dichloromethane [44]. Although the typical peaks of polyurethane and fibroin fall in these regions, not allowing a trustworthy quantitative analysis by deconvolution, this result indicates that the additional washing steps and time associated to the ethanol post-processing treatment were also more effective in removing residual solvents than the simple soaking in methanol.

Figure 10:
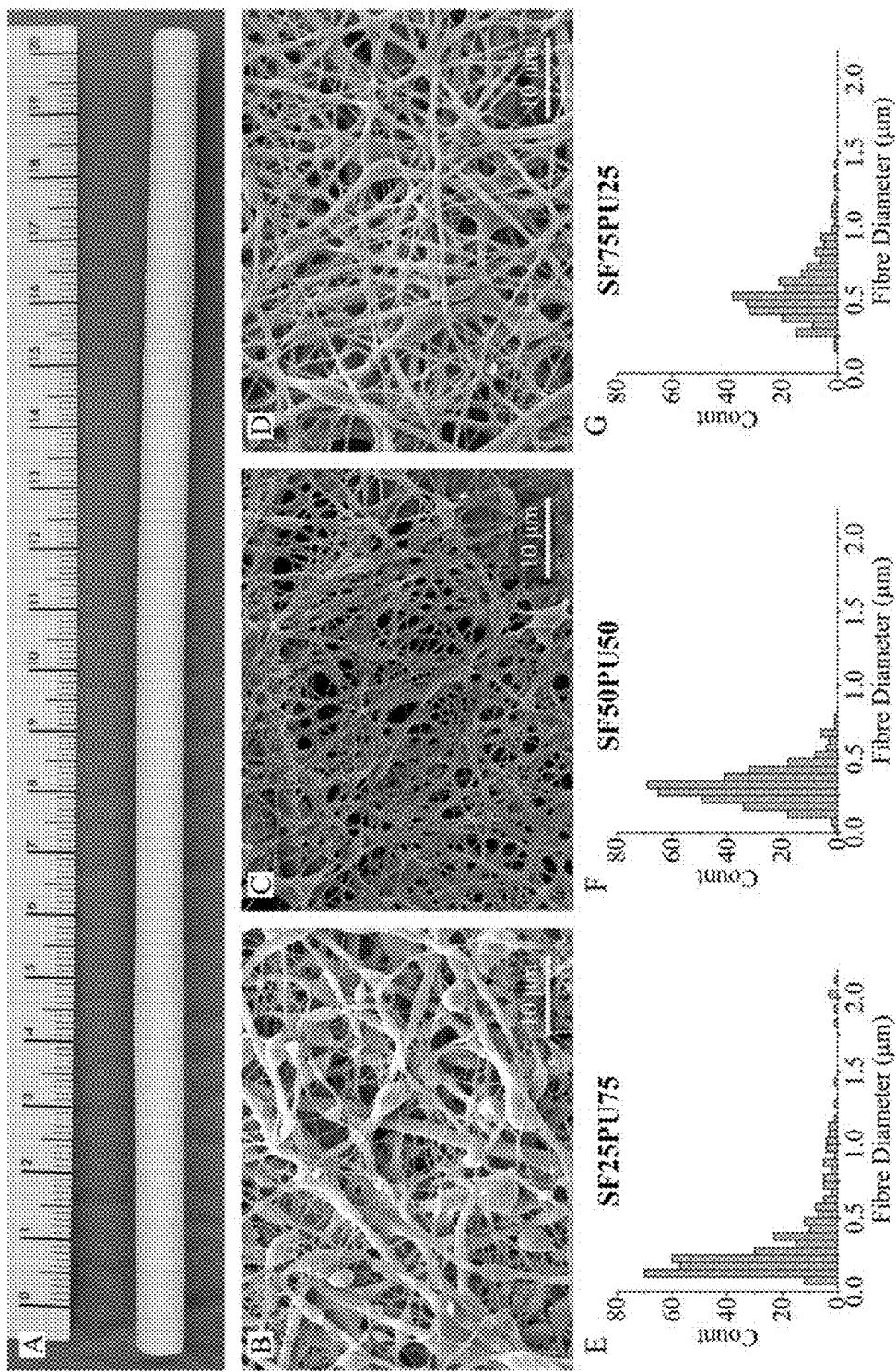
FIG. 10 illustrates structure and morphology of tubular electrospun hybrid meshes composed by a blend of fibroin and polyurethane. A: Macroscopic appearance of an exemplifying SF50PU50 sample (50% silk fibroin and 50% polyurethane). SEM micrographs of samples SF25PU75 (25% silk fibroin and 75% polyurethane) (B), SF50PU50 (C), and SF75PU25 (75% silk fibroin and 25% polyurethane) (D), with a 10 µm scale bar. Histograms represent the fiber diameter analysis of samples SF25PU75 (E), SF50PU50 (F), and SF75PU25 (G).

After assessing the dissolution, blending, electrospinning and post-treatment techniques, the experiments above evaluated the applicability of the proposed process to blends with different respective ratios of fibroin and polyurethane. To this purpose, hybrid tubular meshes were electrospun using solutions with 1:3 (SF25PU75), 1:1 (SF50PU50), 3:1 (SF25PU75) ratios of fibroin and polyurethane. The meshes were characterized in terms of morphology, and, envisioning their possible use as substrates for vascular grafts, the mechanical properties and permeability were also evaluated. SEM micrographs revealed a fibrous morphology mostly at the sub-micrometric level, with virtually indistinguishable, intermingled fibroin/polyurethane fibers (FIG. 10). The fact that fibroin and polyurethane respond to electrospinning and post-processing treatments without undergoing separation and/or delamination, as elsewhere reported for composite/coated scaffolds [30], reassures about the robustness of the proposed technique and suggests that the material could show potential for a gradual in situ remodeling of the fibroin portion of the scaffold, with the polyurethane backbone being incorporated into the newly-formed tissue, sustaining the mechanical properties of the overall implant. Such a stable coalescence between fibroin and polyurethane in all the formulations was confirmed by the uniaxial tensile behavior of the electrospun samples (FIG. 11), which showed a neat and sharp profile, with no signs of the sawtoothed morphology typical of delaminating structures. Mechanical tests also confirmed that increasing the fibroin content in the blend significantly increases the stiffness of the mesh, whereas increasing the polyurethane content in the blend determines an increase in the elongation at break (Table III); this fact shows the possibility of tuning of the mechanical properties of the scaffold to the ones in the implant site, which is known to be a crucial factor especially in the vascular field, where graft-vessel compliance mismatch is recognized as one of the major determinants of grafts' failures [45].

Indeed, samples SF25PU75 and SF50PU50 demonstrated a Young's modulus in line with the values reported in the literature for peripheral arteries, that is, 1-10 MPa, such as the radial and brachial arteries [46-48]. In contrast, our tests revealed that ePTFE has a Young's modulus around 35 MPa; although the literature is inconsistent in reporting the mechanical properties of ePTFE (Young's modulus of tens of MPa [49] to few GPa [50]) possibly due to different types of grafts under study, a clear divergence in mechanical properties is observed when compared with peripheral arteries. Also, no significant difference between the formulations was observed in terms of stress at break, possibly confirming that fibroin and polyurethane are perfectly coalescent within the mesh, and both contribute as load-bearing structures.

Permeability tests (FIG. 12) allowed to verify that the electrospun meshes are characterized by k values (Darcy permeability) in the same order of magnitude ($k \approx 10^{-17}$ $m^2$) as commercially available electrospun polyurethane grafts already used in the clinics (ES PU), hinting at their possibly favorable in situ behavior in terms of avoidance of seroma formation. The measurements also confirmed that ePTFE-containing grafts, known to suffer from scarce integration with the host tissue, are in fact impermeable at 120 mmHg. Finally, the evaluation of permeability after puncture with a dialysis needle (15 G) showed that the behavior of the electrospun meshes is strikingly similar ($k \approx 10^{-13}$ $m^2$) to the one of commercial grafts that are deemed to be suitable for early cannulation (ES PU and 3-layer ePTFE), that is, capable of self-sealing after puncture and avoiding massive bleeding at the puncture site. In summary, herein inventors found a novel blending technique for fibroin and polyurethane, using industrially sustainable solvents (affordable, moderately volatile, addressed by the European Pharmacopoeia), regenerated fibroin and a medical-grade poly-carbonate-urethane suitable for long-term implantation, which proved to be effective in maintaining the characteristic physicochemical features of the two materials. Inventors have also demonstrated the feasibility of electrospinning blend solutions with varying ratios of fibroin and polyurethane, to obtain hybrid tubular meshes possessing extracellular matrix-like nanofibrous morphology, tuneable mechanical properties, and favorable permeability before and after puncture, therefore representing possible substrates for semi-degradable hemodialysis vascular accesses.

REFERENCES

1. Kluin J, Talacua H, Smits A I P M, Emmert M Y, Brugmans M C P, Fioretta E S, Dijkman P E, Sontjens S H M, Duijvelshoff R, Dekker S, Janssen-van den Broek M W J T, Lintas V, Vink A, Hoerstrup S P, Janssen H M, Dankers P Y W, Baaijens F P T, Bouten C V C. In situ heart valve tissue engineering using a bioresorbable elastomeric implant—From material design to 12 months follow-up in sheep. Biomaterials 2017; 125:101-17.
2. Talacua H, Smits A I P M, Muylaert D E P, van Rijswijk J W, Vink A, Verhaar M C, Driessen-Mol A, van Herwerden L A, Bouten C V C, Kluin J, Baaijens F P T. In situ tissue engineering of functional small-diameter blood vessels by host circulating cells only. Tissue Eng Part A 2015; 21:2583-2594.
3. Cattaneo I, Figliuzzi M, Azzollini N, Catto V, Fare S, Tanzi M C, Alessandrino A, Freddi G, Remuzzi A. In vivo regeneration of elastic lamina on fibroin biodegradable vascular scaffold. Int J Artif Organs 2013; 36:166-174.
4. Matsumura G, Nitta N, Matsuda S, Sakamoto Y, Isayama N, Yamazaki K, Ikada Y. Long-term results of cell-free biodegradable scaffolds for in situ tissue-engineering vasculature: In a canine inferior vena cava model. PLoS One 2012; 7:e35760.
5. Rothuizen T C, Damanik F F R, Lavrijsen T, Visser M J T, Hamming J F, Lalai R A, Duijs J M G J, van Zonneveld A J, Hoefer I E, van Blitterswijk C A, Rabelink T J, Moroni L, Rotmans J I. Development and evaluation of in vivo tissue engineered blood vessels in a porcine model. Biomaterials 2016; 75:82-90.
6. Peck M K, Dusserre N, Zagalski K, Garrido S A, Wystrychowski W, Glickman M H, Chronos N A F, Cierpka L, L'Heureux N, McAllister T N. New biological solutions for hemodialysis access. J Vasc Access 2011; 12:185-92.
7. https://www.accessdata.fda.gov/scripts/cdrh/cfdocs/cfcfr/CFRSearch. cfm?fr=878.5030. US Food and Drug Administration. 2017.
8. Santin M, Motta A, Freddi G, Cannas M. In vitro evaluation of the inflammatory potential of the silk fibroin. J Biomed Mater Res 1999; 46:382-389.
9. Meinel L, Hofmann S, Karageorgiou V, Kirker-Head C, McCool J, Gronowicz G, Zichner L, Langer R, Vunjak-Novakovic G, Kaplan D L. The inflammatory responses to silk films in vitro and in vivo. Biomaterials 2005; 26:147-155.
10. Gholipourmalekabadi M, Mozafari M, Bandehpour M, Salehi M, Sameni M, Caicedo H H, Mehdipour A, Hamidabadi H G, Samadikuchaksaraei A, Ghanbarian H. Optimization of nanofibrous silk fibroin scaffold as a delivery system for bone marrow adherent cells: in vitro and in vivo studies. Biotechnol Appl Biochem 2015; 62:785-794.
11. Sakabe H, Ito H, Miyamoto T, Noishiki Y, Ha W S. In vivo blood compatibility of regenerated silk fibroin. Sen'i Gakkaishi 1989; 45: 487-490.
12. Zhang J, Huang H, Ju R, Chen K, Li S, Wang W, Yan Y. In vivo biocompatibility and hemocompatibility of a polytetrafluoroethylene small diameter vascular graft modified with sulfonated silk fibroin. Am J Surg 2017; 213:87-93.
13. Marois Y, Guidoin R. Biocompatibility of polyurethanes. In: Madame Curie Bioscience Database. Austin, Tex.: Landes Bioscience; 2000-2013.
14. Hu J, Chen B, Guo F, Du J, Gu P, Lin X, Yang W, Zhang H, Lu M, Huang Y, Xu G. Injectable silk fibroin/polyurethane composite hydrogel for nucleus pulposus replacement. J Mater Sci Mater Med 2012; 23:711-722.
15. Cai L, Han F, Hu J, Xu G, Huang Y, Lin X. The effect of the preparation process on the swelling behavior of silk fibroin-polyurethane composite hydrogels using a full factorial experimental design. J Polym Eng 2015; 35:523-531.
16. Suzuki Y, Nakazawa Y, Derya A, Komatsu T, Miyazaki K, Yamazaki S, Asakura T. Development of silk/polyurethane small-diameter vascular graft by electrospinning. Seikei-Kakou 2013; 25:181-187.
17. Yu E, Zhang J, Thomson J A, Turng L-S. Fabrication and characterization of electrospun thermoplastic polyurethane/fibroin small diameter vascular grafts for vascular tissue engineering. Int Polym Process 2016; 31:638-46.
18. Park H, Gong M-S, Park J-H, Moon S, Wall I B, Kim H-W, Lee J H, Knowles J C. Silk fibroin-polyurethane blends: Physical properties and effect of silk fibroin content on viscoelasticity, biocompatibility and myoblast differentiation. Acta Biomater 2013; 9: 8962-8971.
19. Shimada K, Higuchi A, Kubo R, Murakami T, Nakazawa Y, Tanaka R. The effect of a silk fibroin/polyurethane blend patch on rat vessels. Organogenesis 2017; 0:1-10.
20. Nakazawa C T, Higuchi A, Asano A, Kameda T, Aytemiz D, Nakazawa Y. Solid-state NMR studies for the development of nonwoven biomaterials based on silk fibroin and polyurethane. Polym J 2017; 49:583-586.
21. Zhou M, Wang W-C, Liao Y-G, Liu W-Q, Yu M, Ouyang C-X. In vitro biocompatibility evaluation of silk-fibroin/polyurethane membrane with cultivation of HUVECs. Front Mater Sci 2014; 8:63-71.
22. Yang H-J, Xu H-Y, Zhu G-C, Ouyang C-X, Wang X-G, Xu W-L. Composite membranes of native silk fibroin powder and biomedical polyurethane for controlled release of heparin. Proc Inst Mech Eng Part H J Eng Med 2011; 225:421-433.
23. Liu X, Zhang C, Xu W, Liu H, Ouyang C. Blend films of silk fibroin and water-insoluble polyurethane prepared from an ionic liquid. Mater Lett 2011; 65:2489-2491.
24. Liu X-Y, Zhang C-C, Xu W-L, Ouyang C. Controlled release of heparin from blended polyurethane and silk fibroin film. Mater Lett 2009; 63:263-265.
25. Um I C, Kweon H Y, Hwang C M, Min B-G, Park Y-H. Structural characteristics and properties of silk fibroin/polyurethane blend films. Int J Ind Entomol 2002; 5:163-170.
26. Liu H, Xu W, Zou H, Ke G, Li W, Ouyang C. Feasibility of wet spinning of silk-inspired polyurethane elastic biofiber. Mater Lett 2008; 62:1949-1952.
27. Bai Z, Xu W, Xu J, Yang H, Xiao S, Liu X, Liang G, Chen L. Fabrication and characterization of silk fibroin powder/polyurethane fibrous membrane. Polym Eng Sci 2012; 52:2025-2032.
28. Tao Y, Yan Y, Xu W, Zhou W. Preparation, structure and properties of blended films of polyurethane and silk fibroin. Acta Polym Sin 2010; 10:27-32.
29. dal Pra I, Petrini P, Charini A, Bozzini S, Fare S, Armato U. Silk fibroin-coated three-dimensional polyurethane scaffolds for tissue engineering: Interactions with normal human fibroblasts. Tissue Eng 2003; 9:1113-1121.
30. Petrini P, Chiarini A, Bozzini S, dal Pra I, Fare S, Armato U. Silk fibroin-polyurethane scaffolds for tissue engineering. J Mater Sci Mater Med 2001; 12:849-853.
31. Chiarini A, Petrini P, Bozzini S, dal Pra I, Armato U. Silk fibroin/poly (carbonate)-urethane as a substrate for cell growth: in vitro interactions with human cells. Biomaterials 2002; 24:789-799.
32. Li J F, Chen Z M, Luo Q, Zhang G H, Wang F P. Preparation and biological properties of nano-silk fibroin/polyurethane/silver nanoparticles composite membranes. Mater Sci Forum 2016; 848:557-566.
33. Luo Z, Zhang Y, Zhou H, Liao J, Zhang X, Wu Q. A one-pot preparation of silk fibroin modified with polyurethane micro-particles. New J Chem 2013; 37:3109.
34. Iizuka E, Sawada K, Motojima K. Physical properties of fibroinblended polyurethane films. J Sericultural Sci Jpn 1998; 67:217-221.
35. European Pharmacopoeia. 8th ed. European Directorate for the Quality of Medicines—Council of Europe; 2014.
36. Tanzi M C, Ambrosio L, Nicolais L, Iannace S, Ghislanzoni L, Mambrito B. Comparative physical tests on segmented polyurethanes for cardiovascular applications. Clin Mater 1991; 8:57-64.
37. Cheng Y-H, Yang S-H, Lin F-H. Thermosensitive chitosan-gelatinglycerol phosphate hydrogel as a controlled release system of ferulic acid for nucleus pulposus regeneration. Biomaterials 2011; 32: 6953-6961.
38. https://www.lubrizol.comNmedia/Lubrizol/Life-Sciences/Documents/TDS/Carbothane-TPU-Clear-Aromatic.pdf. Lubrizol Advanced Materials, Inc. Cleveland, Ohio USA; 2016.
39. Hu X, Kaplan D, Cebe P. Determining beta-sheet crystallinity in fibrous proteins by thermal analysis and infrared spectroscopy. Macromolecules 2006; 39:6161-6170.
40. Park S-H, Gil E S, Mandal B B, Cho H, Kluge J A, Min B-H, Kaplan D L. Annulus fibrosus tissue engineering using lamellar silk scaffolds. J Tissue Eng Regen Med 2012; 6:s24-33.
41. Pignatelli C, Perotto G, Nardini M, Cancedda R, Mastrogiacomo M, Athanassiou A. Electrospun silk fibroin fibers for storage and controlled release of human platelet lysate. Acta Biomater. 2018.
42. Hu X, Shmelev K, Sun L, Gil E S, Park S H, Cebe P, Kaplan D L. Regulation of silk material structure by temperature-controlled water vapor annealing. Biomacromolecules 2011; 12:1686-1696.
43. Vepari C, Kaplan D L. Silk as a biomaterial. Prog Polym Sci 2007; 32: 991-1007.
44. Linstrom P J, Mallard W G, editors. NIST Chemistry webBook, NIST Standard Reference Database Number 69. Gaithersburg Md.: National Institute of Standards and Technology; 2017.
45. Li L, Terry C M, Shiu Y E, Cheung A K. Neointimal hyperplasia associated with synthetic hemodialysis grafts. Kidney Int 2008; 74:1247-1261.
46. Mourad J-J, Girerd X, Boutouyrie P, Laurent S, Safar M, London G. Increased stiffness of radial artery wall material in end-stage renal disease. Hypertension 1997; 30:1425-1430.
47. Bank A J, Kaiser D R, Rajala S, Cheng A. In vivo human brachial artery elastic mechanics: Effects of smooth muscle relaxation. Circulation 1999; 100:41-47.
48. Laurent S, Girerd X, Mourad J J, Lacolley P, Beck L, Boutouyrie P, Mignot J P, Safar M. Elastic modulus of the radial artery wall material is not increased in patients with essential hypertension. Arterioscler Thromb J Vasc Biol 1994; 14:1223-1231.
49. Paasche P E, Kinley C E, Dolan F G, Gozna E R, Marble A E. Consideration of suture line stresses in the selection of synthetic grafts for implantation. J Biomech 1973; 6:253-259.
50. Jorgensen C S, Paaske W P. Physical and mechanical properties of ePTFE stretch vascular grafts determined by time-resolved scanning acoustic microscopy. Eur J Vasc Endovasc Surg 1998; 15: 416-422.

The invention claimed is:
1. A hybrid scaffold suitable for regenerating animal tissues comprising:
peripheral layers made of a material suitable for interfacing with the tissues at the implant site and integrating with the host body cells;
one or more intermediate layers made of combined materials which together are suitable for giving the scaffold mechanical properties suited to withstand the typical stresses in the implantation site and for generating stable coalescence between the layers,
the materials being:
fibroin for the peripheral layers,
a blend of polyurethane and fibroin for each intermediate layer wherein the blend of each intermediate layer comprises electrospun fibroin and electrospun polyure- thane, and whereby the blend inhibits delamination or detachment of the fibroin in the peripheral layers.

2. The hybrid scaffold according to claim 1, wherein each intermediate layer comprises fibroin and polyurethane in complementary weight ratios ranging from 1 to 99%.

3. The hybrid scaffold according to claim 1, wherein the peripheral layers of fibroin have porosity ranging between 1% and 99% and each intermediate layer of fibroin and polyurethane has a porosity ranging between 1% and 99%.

4. The hybrid scaffold according to claim 1, having a tubular shape adapted to the implantation as a vascular prosthesis or to function as a vascular access.

5. The hybrid scaffold according to claim 1, having an element in the form of shapeable lamella suitable for regenerating vascular tissues and the myocardium.

6. The hybrid scaffold according to claim 1, having a shape suitable for replacing a semilunar or atrioventricular valve or parts thereof.

7. The hybrid scaffold according to claim 1, having a shape of a vascular tree, or of a bifurcated vascular tract.

8. The hybrid scaffold according to claim 1, having an assembly of parts forming a heart valve, a part thereof or a bifurcated vascular tract.

9. A process for producing a scaffold according to claim 1, comprising:
   electrospinning a first layer of solubilized fibroin on a collector of a shape suitable-to the desired scaffold to be produced;
   subsequent depositioning on the first layer of one or more overlapping intermediate layers composed of fibroin and polyurethane mixed and/or placed side by side; and
   electrospinning a layer of solubilized fibroin on the one or more intermediate layers, in which said one or more intermediate layers of fibroin and polyurethane is/are produced with the mixture of the two materials solubilized in the following conditions:
a) in a solvent or combination of solvents suitable for solubilizing both or each of the two materials, where denaturations and degradations are avoided, said solvent being selected from the group consisting of water, formic acid, trifluoroacetic acid, chloroform, dichloromethane, hexafluoroisopropanol, dimethylformamide, cyclohexanone, dimethylacetamide, methylene chloride, tetrahydrofuran, dimethylsulfoxide, and mixtures thereof, said solvent optionally including additives to improve the solubilization of the materials;
b) at a concentration suitable to obtain a porosity of the desired scaffold ranging between 1% and 99%,
c) with a sequence of operations suitable to solubilize both fibroin and polyurethane avoiding precipitations,
which causes fibroin and polyurethane to be coalescent in the scaffold.

10. The process according to claim 9, wherein the one or more intermediate layers are composed of fibroin and polyurethane in complementary weight ratios ranging between 1% and 99%.

11. The process according to claim 9, wherein said one or more intermediate layers of fibroin and polyurethane are generated by electrospinning a mixture of fibroin and polyurethane.

12. The process according to claim 9, wherein said one or more intermediate layers of fibroin and polyurethane are generated by electrospinning of distinct fibers of fibroin and polyurethane.

13. The process according to claim 9, wherein said one or more intermediate layers of fibroin and polyurethane are generated by electrospinning of fibroin and polyurethane solutions coaxially arranged with each other.

14. The process according to claim 9, wherein said one or more intermediate layers of fibroin and polyurethane are generated by means of techniques of solvent casting, dipping, particulate leaching, hydrogelation, lyophilization, or additive manufacturing to produce a composite structure of matrix and inclusions, a hydrogel, a sponge or a film with controlled porosity.

15. The process according to claim 9, comprising the electrospinning of a scaffold in separate steps on a composite collector.

16. The process according to claim 9, wherein said one or more intermediate layers of fibroin and polyurethane are produced with a mixture of the two materials where fibroin and polyurethane are solubilized in formic acid and dichloromethane in the ratio 3:2, in the solution the concentration of fibroin is in the range from 0.01% w/v to 98.01% w/v and the concentration of polyurethane is in the range from 0.01% w/v to 98.01% w/v, such mixture being obtained by carrying out the following steps:
   solubilizing of fibroin in two parts of formic acid,
   solubilizing of polyurethane in a combination of one part of formic acid and two parts of dichloromethane, and
   mixing the fibroin solution with the polyurethane solution.

17. The process according to claim 9, wherein the scaffold is subjected to physical-chemical treatments aimed at washing out solvent residuals and/or at inducing fibroin crystallization, that include one or more of the following phases: exposure to organic solvents or to solutions of organic solvents and water or to pure water, application of mechanical stress, thermal treatments.

18. The process according to claim 9, wherein the scaffold is completely or partially subjected to physical-chemical treatments that include one or more of:
   a) coating or functionalization with heparin, warfarin, statin, compounds derived from fish oil, graphite or other carbon-based compounds, anti-thrombin, argatroban, fibronectin, sulphate-based coatings, or treatment with a physical process such as gas plasma and ultraviolet light, in order to improve the properties anti-inflammatory, antiplatelet, anti-thrombotic, and anti-proliferation of smooth muscle cells;
   b) coating or impregnation with albumin or other high molecular weight compounds with the purpose of controlling the permeability of the blood plasma;
   c) coating or functionalization with silver, with antimicrobial peptides or antibiotic and antiviral molecules, or production from fibroin genetically modified, in order to increase the antimicrobial properties.

* * * * *